US008932662B2

(12) United States Patent
Nielsen et al.

(10) Patent No.: US 8,932,662 B2
(45) Date of Patent: Jan. 13, 2015

(54) COATINGS PREPARED FROM POLY(ETHYLENE OXIDE) AND PHOTO-INITATOR-CONTAINING SCAFFOLDS

(75) Inventors: Bo Rud Nielsen, Humlebaek (DK); Carsten Hoj, Vanlose (DK); Christian Benedikt Nielsen, Copenhagen (DK); Niels Jorgen Madsen, Allerod (DK)

(73) Assignee: Coloplast A/S, Humlebaek (DK)

( * ) Notice: Subject to any disclaimer, the term of this patent is extended or adjusted under 35 U.S.C. 154(b) by 1518 days.

(21) Appl. No.: 12/448,195
(22) PCT Filed: Dec. 14, 2007
(86) PCT No.: PCT/EP2007/063984
§ 371 (c)(1),
(2), (4) Date: Jun. 12, 2009
(87) PCT Pub. No.: WO2008/071796
PCT Pub. Date: Jun. 19, 2008

(65) Prior Publication Data
US 2010/0049146 A1    Feb. 25, 2010

(30) Foreign Application Priority Data

Dec. 15, 2006    (WO) ................ PCT/DK2006/000715
Jul. 25, 2007    (WO) ................ PCT/EP2007/057666

(51) Int. Cl.
A61L 33/00    (2006.01)
A61L 17/14    (2006.01)
(Continued)

(52) U.S. Cl.
CPC ............. *A61L 29/085* (2013.01); *A61L 17/145* (2013.01); *C09D 171/02* (2013.01); *C08J 7/123* (2013.01);
(Continued)

(58) Field of Classification Search
USPC ................ 424/445, 70.16; 528/425; 128/640; 523/409
See application file for complete search history.

(56) References Cited

U.S. PATENT DOCUMENTS 4,684,558 A    8/1987    Keusch et al.
5,002,582 A    3/1991    Guire et al.
(Continued)

FOREIGN PATENT DOCUMENTS

EP    0 769 306 A2    4/1997
WO    WO 89/09246    10/1989
(Continued)

OTHER PUBLICATIONS

Kendall et al., Kendall medical product catalog, available online Dec. 8, 2005, pp. 22, https://www.kendallhq.com/kendallhealthcare/pageBuilder.aspx?topicID=69370&breadcrumbs=0:121623, 154342:0,155079:0.*
(Continued)

*Primary Examiner* — Dah-Wei D Yuan
*Assistant Examiner* — Andrew Bowman
(74) *Attorney, Agent, or Firm* — Coloplast Corp., Coloplast A/S; Nick Baumann

(57) ABSTRACT

The application discloses a method for the preparation (by extruding, injection molding or powder coating and subsequent cross-linking by irradiation with UV or visible light) of a medical device element involving a coating composition comprising: a) as the only polymer constituent(s), at least 50% by weight of poly(ethylene oxide)(s) optionally in combination with non-thermoplastic hydrophilic polymer(s), and b) low molecular weight scaffold(s) having a plurality of photo-initiator moieties covalently linked thereto and/or covalently incorporated therein, wherein the photo-initiator moieties constitute 0.01-20% by weight of the combined amount of the poly(ethylene oxide)(s), any non-thermoplastic hydrophilic polymers and the low molecular weight scaffolds. The application further discloses such extruded, injection molded or powder coated medical devices having thereon a layer of a covalently cross-linked coating composition of a poly(ethylene oxide) (PEO), optionally a non-thermoplastic hydrophilic polymer and a low molecular weight scaffold having a plurality of residues of photo-initiator moieties.

12 Claims, 1 Drawing Sheet

(51) Int. Cl.
| | |
|---|---|
| C09D 171/02 | (2006.01) |
| C08J 7/12 | (2006.01) |
| A61L 31/10 | (2006.01) |
| C08L 71/02 | (2006.01) |
| C08J 7/04 | (2006.01) |
| C08G 65/331 | (2006.01) |
| A61L 29/08 | (2006.01) |
| A61L 27/34 | (2006.01) |
| C08L 23/36 | (2006.01) |

(52) U.S. Cl.
CPC .............. *A61L 31/10* (2013.01); *C08L 71/02* (2013.01); *A61L 2400/10* (2013.01); *C08J 7/047* (2013.01); *C08G 65/331* (2013.01); *C08J 2471/00* (2013.01); *C08L 23/36* (2013.01); *A61L 27/34* (2013.01)
USPC ......... 427/2.1; 424/445; 424/70.16; 528/425; 523/409

(56) References Cited

U.S. PATENT DOCUMENTS

| | | | |
|---|---|---|---|
| 5,061,424 | A | 10/1991 | Karimi et al. |
| 5,084,315 | A | 1/1992 | Karimi et al. |
| 5,143,071 | A * | 9/1992 | Keusch et al. ............ 600/397 |
| 5,225,460 | A * | 7/1993 | Sampath et al. .......... 523/409 |
| 5,263,992 | A | 11/1993 | Guire |
| 6,447,835 | B1 | 9/2002 | Wang et al. |
| 6,790,519 | B1 | 9/2004 | Johnson et al. |
| 7,276,247 | B2 | 10/2007 | Fansler et al. |
| 2003/0147835 | A1 * | 8/2003 | Munro et al. ............ 424/70.16 |
| 2004/0062793 | A1 * | 4/2004 | Dyke ...................... 424/445 |
| 2005/0070688 | A1 * | 3/2005 | Lewandowski et al. ...... 528/425 |

FOREIGN PATENT DOCUMENTS

| | | |
|---|---|---|
| WO | WO 03/086493 A1 | 10/2003 |
| WO | WO 2005/035607 A1 | 4/2005 |
| WO | WO 2005/079883 A1 | 9/2005 |
| WO | WO 2005/092402 A1 | 10/2005 |

OTHER PUBLICATIONS

Dimitrov et al., Preparation and Characterixation of Polyethylene Oxide Hydrogels with Cytisine, 2004, Acta Pharmaceutica Turcica, vol. 46, pp. 49-54.*

Gilbert A., et al., "Essentials of Molecular Photochemistry", Blackwell, London, pp. 310-311, 1991.

Gould, M.L., et al., "Novel Self-Initiating UV-Curable Resins: Generation Three," Proceedings from RadTech Europe 05, Barcelonia Spain, vol. 1, pp. 245-251, Oct. 18-20, 2005.

Nguyen, C.K., et al., "Maleimide Reactive Oligomers," Proceedings from RadTech Europe 03, Berlin, Germany, vol. 1., pp. 589-594, Nov. 3-5, 2003.

Fouassier, J.P., et al., "Excited-State Reactivity in Radical Polymerisation Photoinitiators," London, Elsevier, vol. II, pp. 1-61, 1993.

Kopeinig, S., et al., "Further Covalently Bonded Photoinitiators," Proceedings from RadTech Europe 05, Barcelonia, Spain, vol. 2, pp. 375-381, Oct. 18-20, 2005.

March, J., et al., "Advanced Organic Chemistry," Reaction, Mechanisms and Structure, Wiley-Interscience, $3^{rd}$ ed., pp. 377-379, New York, 1985.

March, J., et al., "Advanced Organic Chemistry," Reaction, Mechanisms and Structure, Wiley-Interscience, $3^{rd}$ ed., pp. 484-487, New York, 1985.

March, J., et al., "Advanced Organic Chemistry," Reaction, Mechanisms and Structure, Wiley-Interscience, $3^{rd}$ ed., pp. 636-637, New York, 1985.

Walling, C., et al., "Free Radical Additions to Olefins to Form Carbon-Carbon Bonds," Organic Reactions, vol. 13, pp. 91-149 (1963).

Leon, J.A., et al., "UV-Light Sensitive (LS®) Urethane Acrylate Oligomers," RadTech Europe 2005, Barcelona, Spain, vol. 2, pp. 359-364, Oct. 18-20, 2005.

* cited by examiner

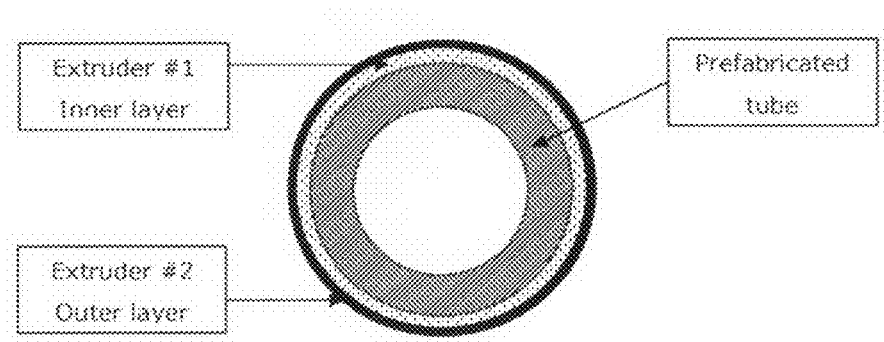

US 8,932,662 B2

COATINGS PREPARED FROM POLY(ETHYLENE OXIDE) AND PHOTO-INITATOR-CONTAINING SCAFFOLDS

This is a national stage of PCT/EP07/063984 filed Dec. 14, 2007 and published in English, which has a priority of Denmark no. PCT/DK06/000715 filed Dec. 15, 2006 and a priority of European no. PCT/EP07/057666 filed Jul. 25, 2007, hereby incorporated by reference.

FIELD OF THE INVENTION

The present invention relates to a method for the preparation of a medical device element by means of extrusion, injection moulding or powder coating. The invention further relates to medical devices comprising such extruded, injection moulded or powder coated medical device elements. The medical device elements are characterized by a prefabricated shaped article or a thermoplastic substrate polymer having thereon a layer of a covalently cross-linked coating composition of a poly(ethylene oxide) (PEO), optionally a non-thermoplastic hydrophilic polymer and a low molecular weight scaffold having a plurality of residues of photo-initiator moieties covalently linked thereto and/or covalently incorporated therein.

BACKGROUND OF THE INVENTION

Many medical devices require a lubricated surface. In the medical field, simple devices such as, for example, catheters, guide wires, etc., must be inserted into a body cavity or through the skin and at a later time be withdrawn. Patient treatment often includes catheterization procedures or nutrition delivery systems, most of which involve invasive techniques. In all such cases, effective lubrication which is stable throughout both the insertion and withdrawal stages of the procedure contributes greatly to patient comfort.

U.S. Pat. No. 5,084,315 discloses a method for preparing a shaped article, e.g. by co-extrusion, utilizing a composition including PEO and a polyurethane, which is not covalently cross-linked. The surface of the article is said to be lubricious when contacted with water.

U.S. Pat. No. 6,447,835 discloses a method of preparing a coated hollow polymeric tubular member for a medical device by co-extruding the tube together with a coating.

The coating may comprise poly(ethylene oxide). The coating may also comprise acrylic monomers which may be reacted to form a cross-linked acrylic polymer network after extrusion.

U.S. Pat. No. 4,684,558 discloses methods for making adhesive cross-linked poly(ethylene oxide) hydrogel sheets by cross-linking with electron beam radiation.

U.S. Pat. No. 6,790,519 B1 and WO 2005/079883 A1 disclose a method for making cross-linked poly(ethylene oxide) hydrogels by grafting silanol-containing moieties onto a poly(ethylene oxide) chain. Cross-linking between poly(ethylene oxide) chains occurs by condensation reactions between silanol groups.

U.S. Pat. No. 7,276,247 B2 discloses a method for cross-linking by UV-irradiation of unsaturated functionalities present in poly(ethylene oxide) chains by having photo-initiators pendant on other poly(ethylene oxide) chains.

WO 03/086493 A1 and WO 2005/092402 disclose a method for cross-linking by UV-irradiation of unsaturated functionalities present in poly(ethylene oxide) chains by having photo-initiators and unsaturated functionalities present as end-groups in the poly(ethylene oxide) chains.

WO 2005/035607 A1 further discloses a method for making hydrophilic poly(ethylene oxide) compositions prepared by cross-linking by means of UV-irradiation of unsaturated functionalities present in poly(ethylene oxide) chains and having photo-initiators pendant on other poly(ethylene oxide) chains.

SUMMARY OF THE INVENTION

The before-mentioned prior art documents mainly solves the problem of cross-linking poly(ethylene oxide)s by means of radical polymerisation of unsaturated functionalities.

The present invention provides an alternative route involving the application of a particular scaffold having a plurality of photo-initiator moieties covalently linked thereto and/or covalently incorporated therein. Hence, the present invention i.a. provides a method for the preparation of medical devices which provides advantages with respect to simplicity and which provides advantages with respect to exceptionally low friction, excellent cohesion and excellent adhesion.

Hence, the present invention provides a method for the preparation of a medical device element involving poly(ethylene oxide) and a low molecular weight scaffold having a plurality of photo-initiator moieties covalently linked thereto and/or covalently incorporated therein, cf. claim 1.

Moreover, the present invention also provides various medical devices as defined in claims 12, 13 and 14.

BRIEF DESCRIPTION OF THE DRAWING

FIG. 1 illustrates a medical device (e.g. a tube of catheter) of a prefabricated tube, a layer of a thermoplastic substrate polymer, and a covalently cross-linked coating composition.

DETAILED DESCRIPTION OF THE INVENTION

The Method of the Invention

As mentioned above, the present invention relates to a method for the preparation of a medical device element, said method comprising the steps of:
(i) providing a prefabricated shaped article and/or a thermoplastic substrate polymer;
(ii) providing a coating composition comprising:
 (a) as the only polymer constituent(s), one or more poly(ethylene oxide)s optionally in combination with one or more non-thermoplastic hydrophilic polymers, said one or more poly(ethylene oxide)s constituting at least 50% by weight of said polymer constituent(s), and
 (b) one or more low molecular weight scaffolds having a plurality of photo-initiator moieties covalently linked thereto and/or covalently incorporated therein,
 wherein the photo-initiator moieties constitute 0.01-20% by weight of the combined amount of the one or more poly(ethylene oxide)s, any non-thermoplastic hydrophilic polymers and the one or more low molecular weight scaffolds;
(iii) extruding, injection moulding or powder coating the coating composition of step (ii) on the prefabricated shaped article and/or the thermoplastic substrate polymer of step (i) so as to provide the medical device element of said prefabricated shaped article and/or said substrate polymer having thereon a layer of said coating composition, wherein, when both of said prefabricated shaped article and said substrate polymer are present, said prefabricated shaped article has thereon a layer of said substrate polymer;

(iv) irradiating the coating composition with UV or visible light so as to covalently cross-link said coating composition.

In a first main aspect of the invention, the one or more poly(ethylene oxide)s are the only polymer constituent(s) of the coating composition.

The invention is based on the finding that cross-linking of the specific coating composition subsequent to extrusion, injection moulding or powder coating by means of one or more photo-initiator(s) and UV or visible light provides medical device elements which have: good adhesion of the coating composition (including the poly(ethylene oxide) (PEO)) to the prefabricated shaped article or the substrate polymer; good cohesion of the coating composition; and good water-retention of the poly(ethylene oxide) (PEO) and any non-thermoplastic hydrophilic polymers in the wet state and thereby excellent properties with respect to low friction for an extended period of time. Contrary to most of the hitherto known methods, the method of the present invention is completely independent of cross-linking and polymerisation by means of ethylenically unsaturated moieties (e.g. acrylate, methacrylate or vinyl moieties); in fact, the coating composition is preferably completely devoid of any ethylenically unsaturated moieties, in particular acrylate, methacrylate and vinyl moieties.

The good properties with respect to good water-retention of the coating and excellent properties with respect to low friction for an extended period of time is somewhat contradictory to the fact the flexibility of the PEO chains will be restricted by means of the cross-linking of the polymer and anchoring to the substrate polymer or prefabricated shaped article. However, the thermoplastic nature of PEO together with extreme hydrophilic and friction reducing properties renders PEO particularly suited in the methods and products of the present invention. Moreover, the presentation of the photo-initiator moieties as covalently linked to and/or covalently incorporated in a scaffold appears to further facilitate the above-mentioned useful properties.

Medical Device

The term "medical device" should be interpreted in a fairly broad sense. Suitable examples of medical devices (including instruments) are catheters (such as urinary catheters), endoscopes, laryngoscopes, tubes for feeding, tubes for drainage, endotracheal tubes, guide wires, sutures, cannulas, needles, thermometers, condoms, urisheaths, barrier coatings e.g. for gloves, stents and other implants, contact lenses, extra corporeal blood conduits, membranes e.g. for dialysis, blood filters, devices for circulatory assistance, condoms, dressings for wound care, and ostomy bags. Most relevant are catheters, endoscopes, laryngoscopes, tubes for feeding, tubes for drainage, guide wires, sutures, and stents and other implants. Particularly interesting medical devices within the context of the present invention are catheters, such as urinary catheters.

It is also envisaged that the method of the invention is equally useful for the preparation of devices with low-friction surfaces for non-medical purposes, e.g. packaging for foodstuff, razor blades, fishermen's net, conduits for wiring, water pipes having a coating inside, sports articles, cosmetic additives, mould release agents, and fishing lines and nets. Hence, in a further alternative aspect of the invention, the method and devices presently described and claimed can be modified so as to cover such possibilities.

Some medical devices may be constructed of one or more medical device elements which, when being assembled or rearranged, represent the ready-to-use medical device. Reference to a "medical device element" and "catheter element" means the medical device or catheter as such (i.e. one piece medical device or catheter) or a part of a "ready-to-use" medical device or catheter.

Medical device elements are in the present context formed from a prefabricated shaped article and/or a thermoplastic substrate polymer and a coating composition. Upon (co)extrusion or injection moulding of the prefabricated shaped article and/or the thermoplastic substrate polymer and the simultaneous or subsequent application of the coating composition by co-extrusion, injection moulding or powder coating, at least a part of the surface of the prefabricated shaped article or the thermoplastic substrate polymer becomes coated with the coating composition as will be explained in more detail in the following. In some embodiments, the coating composition (i.e. a hydrophilic coating) is covering the full (outer) surface of the prefabricated shaped article/substrate polymer, and in some other embodiments, only to a part of the surface thereof. In the most relevant embodiments, the coating composition covers at least a part of the surface (preferably the whole surface) of the medical device that—upon proper use—comes into direct contact with body parts for which the medical device is intended.

Prefabricated Shaped Articles

In the embodiments where a prefabricated shaped article is involved, the method is designed to provide a coating onto such as shaped article. A wide variety of shaped articles are envisaged (e.g. tubes, wires, lines, stents, catheters, guides, endodontic and orthodontic instruments, needles, trocars for e.g. laparoscopic surgery, laparoscopic accessories, surgical instruments, guide wires), just as a number of different materials may constitute such shaped articles, such as metals and alloys, e.g. stainless steel cores or typical guide-wire alloys, e.g. Ti alloys such as Nitinol and pseudoplastic Beta Ti—Mo—V—Nb—Al alloys. Glasses and ceramics just as thermoplastic polymers are also envisaged. Suitable materials also include: Thermoplastic polymers such as hydrophilic polyurethanes, hydrophobic polyurethanes, polyether block amides (e.g. Pebax™), PVC, polyamides, polyesters, biodegradable polyesters, polyacrylates, PS, silicones, latex rubber; block copolymers with the different structures diblock (A-B), multiblock $(A-B)_n$ or triblock (A-B-A) such as SEBS, SIS, SEPS, SBS, SEEPS (the block copolymers may be grafted with maleic anhydride onto the rubber block, typically the mid-block for triblock copolymers); thermoplastic polymers such as LDPE, LLDPE, VLDPE, PP, PE, and copolymers of ethylene and propylene, metallocene polymerized polyolefins, PS, EMA, EEA, EnBA, PE g-MAH, EVA, EVOH and vinyl acetate copolymer grafted with maleic anhydride (EVA g-MAH), or combinations thereof e.g. Orevac® ethylene-vinyl acetate-maleic anhydride terpolymers; and the functional polyolefins range, such as Lotader® ethylene-acrylic ester terpolymers with either MAH or GMA; and the maleic anhydride grafted polymers of PE, PP, PS, etc. The abbreviations are explained in the Table in the Examples.

In order to improve and obtain a proper surface anchoring between different layers on prefabricated shaped articles there will be several strategies. In some cases di- or triblock copolymers with one or more polyolefinic groups together with more polar PS block(s) can give an optimal surface anchoring between layers. Otherwise the substrate polymer can be modified during reactive polymer blending where functional groups on the polymers can be utilized to combine non-polar polymers with polar or hydrophilic polymers.

Reactive polymer blending can also be used to obtain covalent bonding between photo-initiators and non-polar, polar or hydrophilic functional polymers in order to improve surface anchoring during a photo-curing after a co-extrusion of the coatings.

Thermoplastic Substrate Polymer

In the embodiments where a thermoplastic substrate polymer is involved, the method is designed to provide a coating onto this substrate. The thermoplastic substrate polymer is selected so as to provide the physical shape of the medical device element or so as to provide a suitable interface between the coating composition and the prefabricated shaped article. Hence, the substrate polymer is typically selected from polyurethanes, polyether block amides (e.g. Pebax™), PVC, polyamides, polyesters, polyacrylates, PS, silicones, latex rubber, SEBS, SIS, SEPS, SEEPS, EVA, PE, and copolymers of ethylene and propylene; thermoplastic polymers such as hydrophilic polyurethanes, hydrophobic polyurethanes, polyether block amides (e.g. Pebax™), PVC, polyamides, polyesters, polyacrylates, PS, silicones, latex rubber; block copolymers with the different structures diblock (A-B), multiblock $(A-B)_n$ or triblock (A-B-A) such as SEBS, SIS, SEPS, SBS, SEEPS; the block copolymers maybe grafted with MAH onto the rubber block, typically the mid-block for triblock copolymers; thermoplastic polymers such as LDPE, LLDPE, VLDPE, PP, PE, and copolymers of ethylene and propylene, metallocene polymerized polyolefins, PS, EMA, EEA, EnBA, PE g-MAH, EVA, EVOH and EVA g-MAH, or combinations thereof, e.g. Orevac® ethylene-vinyl acetate-maleic anhydride terpolymers; the functional polyolefins range, such as Lotader® ethylene-acrylic ester terpolymers with either MAH or GMA; maleic anhydride grafted polymers of PE, PP, PS, etc.; and the EPOCROS K-series of reactive acrylate-oxazoline copolymers or the RPS/RAS-series of styrene-oxazoline copolymers, or styrene-acrylonitril-oxazoline copolymers.

Currently very relevant materials for use as the thermoplastic substrate polymer are polyurethanes and PVC, in particular polyurethanes, e.g. hydrophobic polyurethanes.

Coating Composition

The principal constituents of the coating composition are the poly(ethylene oxide)s (PEOs) (in the first main aspect of the invention in fact being the only polymer of the composition) and the low molecular weight scaffold(s) having a plurality of photo-initiator moieties covalently linked thereto and/or covalently incorporated therein. The one or more poly(ethylene oxide)s may in the second main aspect of the invention be used in combination with one or more non-thermoplastic hydrophilic polymers. These constituents will be discussed in detail further below.

Depending on the intended use, additives may be incorporated into the coating composition in order to achieve particular properties. For example one or more additives such as flow aids, flatting agents, heat stabilizers, surface cure modifiers, antibacterial agents, and osmolality increasing compounds may be added to the coating composition. Such additives and their use to modify polymer properties are conventional and well known to those skilled in the art. Such other components may be used in an amount of up to 10% by weight, e.g. up to 5% by weight, of the coating composition.

The antibacterial agent may be a silver salt, e.g. silver sulphadiazine; an acceptable iodine source such as povidone iodine (also called PVP iodine); chlorhexidine salts such as the gluconate, acetate, hydrochloride or the like; or salts or quaternary antibacterial agents such as benzalkonium chloride or other antiseptics or antibiotics. Antibacterial agents reduce the risk of infection, e.g. when urodynamic examinations are performed.

For medical devices or instruments suitable for introduction into human cavities, it may be advantageous to include an osmolality increasing compound, e.g. a water-soluble non-ionic compound such as glucose, sorbitol, glycerin, or urea; or ionic compounds such as halides, nitrates, acetates, citrates or benzoates of alkali metals or alkaline earth metals or silver; or carboxylic acids such as acetic acid, etc.

It may further be desirable to include a plasticizer in the coating composition in order to facilitate the extrusion, injection moulding or powder coating. In such instances, a plasticizer may be included in an amount of up to 10% by weight of the coating composition. Examples of such plasticizers include carboxylic acid-based plasticizers, such as partially esterified citric acids obtained from Jungbunzlauer and such citric acid esters obtained from Grindsted products, e.g. GRINDSTED-CITREM. It should be understood that plasticizers within the present context are generally to be understood as low-molecular weight constituents.

As it will be evident from the description below, the present invention takes advantage of a covalent cross-linking method which does not require cross-linking by means of (meth) acrylate monomers, and the coating composition does therefore in the most interesting embodiments not comprise (meth) acrylic monomers. Residual acrylates may be acutely toxic, genotoxic, carcinogenic, or they may cause allergy, skin rashes, sensitization or, at best, be only locally irritating. Hence systems with residual ethylenically unsaturated monomers, e.g. acrylates or other reactive monomers, are best avoided.

In one embodiment, the coating composition preferably consists of:
20-99.99% by weight of the one or more poly(ethylene oxide)s (PEO),
0-10% by weight of one or more plasticizers,
0.01-80% by weight of the one or more low molecular weight scaffolds, and
0-5% by weight of other components.

In a more interesting embodiment, the coating composition consists of:
30-99.9% by weight of the one or more poly(ethylene oxide)s (PEO),
0-5% by weight of one or more plasticizers,
0.1-70% by weight of the one or more low molecular weight scaffolds, and
0-5% by weight of other components.

In a particular embodiment, the coating composition consists of:
40-99% by weight of the one or more poly(ethylene oxide)s (PEO),
1-60% by weight of the one or more low molecular weight scaffolds, and
0-5% by weight of other components.

In another particular embodiment, the coating composition consists of:
50-99% by weight of the one or more poly(ethylene oxide)s (PEO),
0-10% by weight of one or more plasticizers,
1-50% by weight of the one or more low molecular weight scaffolds, and
0-5% by weight of other components.

In a further embodiment, the coating composition consists of:
40-94% by weight of the one or more poly(ethylene oxide)s (PEO),
5-30% by weight of the one or more non-thermoplastic hydrophilic polymers,
0-10% by weight of one or more plasticizers, 1-40% by weight of the one or more low molecular weight scaffolds, and 0-5% by weight of other components.

Poly(Ethylene Oxide) (PEO)

The coating composition comprises—as one of the principal constituents—one or more poly(ethylene oxide)s.

The term "polymer" (e.g. as referring to the poly(ethylene oxide)s and the non-thermoplastic hydrophilic polymer) signifies an organic compound having repeating units and having a weight average molecular weight of more than 10 kDa (10,000 g/mol). Conversely (and complementary hereto), the term "scaffold" or "low molecular weight scaffold" signifies an organic compound to which the photo-initiator moieties are covalently bonded and which has a weight average molecular weight (without the photo-initiator moieties) of up to 10 kDa (g/mol).

The main requirement to the poly(ethylene oxide)(s) is to ensure that the covalently cross-linked coating composition becomes very slippery when it is swollen with hydrophilic liquids such as water or glycerol. Hence, the main function of the PEO(s) is to give the swollen coating low friction and high water-retention.

The weight average molecular weight ($M_w$) of the poly(ethylene oxide) (PEO) is above 10,000 Da (g/mol). In practice, the PEO may be of any suitable weight average molecular weight ($M_w$), but preferably in the range of 100,000 to 8,000,000 Da (g/mol), most preferably 200,000 to 4,000,000 Da (g/mol). Suitable PEOs may be purchased from Dow under the trade name Polyox®.

It is important to note, that the poly(ethylene oxide)s do not carry any ethylenically unsaturated functionalities, such as acrylate moieties, methacrylate moieties, or vinyl moieties, etc. On the contrary, the cross-linking of the coating composition and in particular the poly(ethylene oxide)s is based on other mechanisms.

In the first main aspect of the invention, the one or more poly(ethylene oxide)s are the only polymer constituents of the composition. Hence, it should be understood that the poly(ethylene oxide)s thereby constitute 100% by weight of the polymer constituents.

Non-Thermoplastic Hydrophilic Polymers

In the second main aspect of the invention, the polymer constituents are one or more poly(ethylene oxide)s in combination with one or more non-thermoplastic hydrophilic polymers, wherein the one or more poly(ethylene oxide)s constitutes at least 50% by weight of the total amount of polymer constituents.

Preferably, the one or more poly(ethylene oxide)s constitutes 50-98%, e.g. 55-90%, or 60-85%, by weight of the total amount of polymer constituents, whereas the non-thermoplastic hydrophilic polymer(s) constitute the remaining part, i.e. 2-50%, e.g. 10-45%, or 15-40%, by weight of the total amount of polymer constituents. It is believed that the thermoplastic properties of the one or more poly(ethylene oxide)s will provide sufficient flow properties for the total coating composition, including the non-thermoplastic hydrophilic polymers and the scaffold, so that the coating composition becomes very useful for extrusion, injection moulding and powder coating applications.

Although the non-thermoplasticity of the hydrophilic polymers is the only general requirement, it is believed that particularly useful non-thermoplastic hydrophilic polymers are those selected from the group consisting of poly(N-vinyl pyrrolidone), poly(acrylic acid), polyoxazoline, and copoly(methyl vinyl ether/maleic anhydride).

Scaffolds Having Photo-Initiator Moieties Covalently Linked Thereto and/or Covalently Incorporated Therein The coating composition further comprises—as one of the principal constituents—one or more low molecular weight scaffolds having a plurality of photo-initiator moieties covalently linked thereto and/or covalently incorporated therein.

The scaffold may be chosen from a wide range of linear, branched, cyclic and dendritic molecular species, i.e. the photo-initiator moieties are "covalently linked" to such scaffolds. It should be possible to attach a plurality of (i.e. at least two) photo-initiator moieties to the scaffold(s) by covalent bonds. Moreover, the scaffold may be in the form of two or several scaffold fragments which are held together by photo-initiator moieties, i.e. the photo-initiator moieties are "covalently incorporated" into the backbone of the scaffold. It can easily be envisaged that scaffolds may have photo-initiator moieties covalently linked thereto and at the same time may have photo-initiator moieties covalently incorporated therein.

An illustrative example of a scaffold having photo-initiator moieties covalently linked thereto is e.g.:

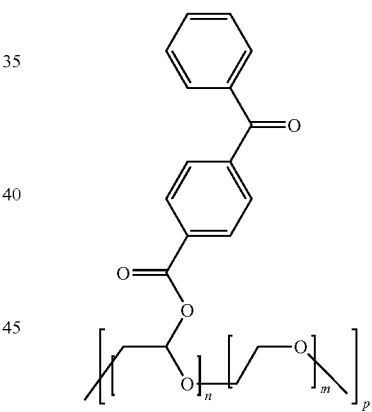

An illustrative example of a scaffold having photo-initiator moieties covalently incorporated in the backbone thereof is e.g.:

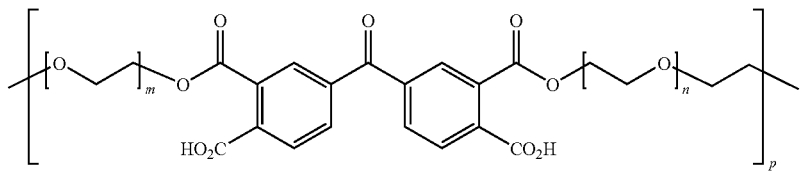

The scaffold should be capable of having covalently linked thereto and/or covalently incorporated therein a plurality of photo-initiator moieties. The "plurality" of photo-initiator moieties means at least two photo-initiator moieties, but in some instances more than two (e.g. three, four, five, six or even more) photo-initiator moieties.

In some currently preferred embodiments, the scaffold has at least three photo-initiator moieties covalently linked thereto and/or covalently incorporated therein With respect to the "loading" of photo-initiator moieties, the photo-initiator moieties constitute 0.01-20% by weight, such as 0.05-15% of the combined amount of the one or more poly(ethylene oxide)s, any non-thermoplastic hydrophilic polymers and the one or more low molecular weight scaffolds (including the photo-initiator moieties).

The term "low molecular weight" refers to a scaffold (without the photo-initiator moieties) having in itself a weight average molecular weight ($M_w$) of up to 10 kDa (10,000 g/mol). Preferably, the weight average molecular weight of the scaffold is in the range of 50-10,000 Da (g/mol), such as 100-10,000 Da (g/mol), in particular 250-8,000 Da (g/mol) or 500-10,000 Da (g/mol). It should be understood that weight average molecular weight of the "scaffold" refers to the weight of the scaffold without the photo-initiator moieties, or the total weight of the scaffold fragments without the photo-initiator moieties, whatever the case may be.

If the scaffold is in the form of two or more scaffold fragments, it is furthermore preferred that each of the fragments has a molecular weight of at least 50 g/mol, such as at least 100 g/mol.

It has proved to be advantageous to include photo-initiator moieties which are covalently linked to and/or covalently incorporated into a low molecular weight scaffold in the coating composition in order to ensure that the photo-initiator moieties are homogeneously distributed within the coating composition. Moreover, it turns out that by covalently combining the photo-initiator moieties with a scaffold (possibly in the form of two or several scaffold fragments), the subsequent migration of the photo-initiator moieties is markedly reduced. Moreover, it appears that photo-initiator moieties which for some reason remain unreacted after the irradiation will not migrate out of the resulting coating.

In one embodiment of the present invention, the scaffold has a plurality (e.g. at least three) of photo-initiator moieties covalently linked thereto.

In another embodiment of the present invention, the scaffold has a plurality (e.g. at least three) of photo-initiator moieties covalently incorporated therein.

In a third interesting embodiment of the present invention, the scaffold has a plurality (e.g. at least three) of photo-initiator moieties, at least one being covalently linked thereto and at least one being covalently incorporated therein.

Although the scaffold may be based on a wide range of structures, including oligomers and low-molecular weight polymers ($M_w$<10,000), it is currently believed that particularly useful scaffolds are those selected from polyethylene glycols, poly(styrene-co-maleic anhydride)s, aliphatic polyether urethanes, polyetheramines (e.g. Jeffamines from Huntsman), and polyesters.

The scaffold(s) may be either hydrophilic or hydrophobic or both (i.e. amphiphilic). Preferably the scaffold(s) are compatible with the polymer constituent(s) in order to ensure perfect homogeneity and hence a uniform spatial distribution of the attached photo-initiator moieties in the coating composition. If a uniform distribution of the photo-initiator moieties in the coating composition can be achieved, then the amount of photo-initiator and/or the UV irradiation time necessary for curing is minimal.

Some commercially available scaffolds with a weight average molecular weight of less than 10 kDa are listed below. These scaffolds are available from the Sigma-Aldrich Chemical Company, except where otherwise stated. Some scaffolds are listed in more than one category.

Nucleophilic scaffolds containing hydroxyl or amino groups, either as end groups or in the backbone, include: PVOH, poly(diethylene glycol/trimethylolpropane-alt-adipic acid), poly(diethylene glycol/glycerol-alt-adipic acid), PEG, [di{poly(ethylene glycol)}adipate], poly(ethylene glycol-ran-propylene glycol), poly(ethylene glycol)-block-poly(propylene glycol)-block-poly(ethylene glycol), poly(propylene glycol)-block-poly(ethylene glycol)-block-poly(propylene glycol), poly(propylene glycol), poly(tetrahydrofuran), [polycaprolactone diol], [polycaprolactone triol], [poly(diethylene glycol phthalate) diol], poly(4-hydroxystyrene), [polybutadiene, dihydroxyl terminated], [HPEU with hydroxyl end groups], [polyurethane diol solution (proprietary Aldrich product)], sugars, dextrans, pullulans, chitosan oligosaccharide lactate, gelatins (from Fibrogen), hydroxypropyl methylcellulose, [poly(tetrahydrofuran), bis(3-amino-1-propyl) terminated], [poly(ethyleneimine), ethylenediamine end-capped], [poly(propylene glycol)-block-poly(ethylene glycol), bis(3-amino-1-propyl) terminated], [poly(propylene glycol)-block-poly(ethylene glycol)-block-poly(propylene glycol), bis(2-amino-1-propyl) terminated], and [poly(propylene glycol), bis(2-amino-1-propyl) terminated]. Notably, dendritic polyols such as Boltorn H20, Boltorn H30 and Boltorn H40 (from Perstorp), and Starburst, Priostar DNT-2210 and Priostar DNT-2211 (from Dendritic Nanotechnologies) constitute very good scaffolds for the present invention. Dendritic polyamines such as the Starburst series, Priostar DNT-2200 and Priostar DNT-2201 (from Dendritic Nanotechnologies) also constitute good scaffolds for the invention. Hyperbranched polynucleophiles may also be used.

Electrophilic scaffolds containing carboxylic acids, anhydrides or isocyanate groups, either as end groups or in the backbone, include: Poly(acrylic acid), [poly(acrylic acid) sodium salt], [poly(methacrylic acid) sodium salt], [poly(styrenesulfonic acid) sodium salt], poly(acrylic acid-co-maleic acid), [poly(acrylonitrile-co-butadiene-co-acrylic acid), dicarboxy terminated], polystyrene-block-poly(acrylic acid), gelatins (from Fibrogen), [poly(ethylene glycol), di(carboxymethyl) terminated], [poly(acrylonitrile-co-butadiene), dicarboxy terminated], [polybutadiene, dicarboxy terminated], poly(isobutylene-alt-maleic anhydride), [poly(ethylene adipate), tolylene 2,4-diisocyanate terminated], and [poly(propylene glycol), tolylene 2,4-diisocyanate terminated]. Dendritic polycarboxylic acids such as the Starburst series, Priostar DNT-2220 and Priostar DNT-2221 (from Dendritic Nanotechnologies) also constitute good scaffolds for the invention. Hyperbranched polyelectrophiles may also be used.

Scaffolds suitable for transesterification and transamidation include: Poly(methyl methacrylate), poly(ethyl methacrylate), poly(butyl methacrylate), and poly(tert-butyl methacrylate).

Scaffolds containing acylatable, electron-rich aromatic systems include: Polystyrene-block-poly(acrylic acid), poly (2-vinylpyridine), poly(2-vinylcarbazole), polycarbonate, poly(α-methylstyrene), polystyrene, poly(2-vinyinaphthalene), and polyacenaphthylene.

Scaffolds containing graftable ether linkages: PEG, HPEU, [di{poly(ethylene glycol)}adipate], poly(ethylene glycol-ran-propylene glycol), poly(ethylene glycol)-block-poly(propylene glycol)-block-poly(ethylene glycol), poly(propylene glycol)-block-poly(ethylene glycol)-block-poly (propylene glycol), poly(propylene glycol), poly(tetrahydrofuran), and [poly(diethylene glycol phthalate) diol].

Further nucleophilic scaffolds with a weight average molecular weight of less than 10 kDa, may be formed by radical homopolymerization, random copolymerisation or block copolymerisation of at least one of the monomers 2-hydroxyethyl acrylate, 2-hydroxyethyl methacrylate, and 4-hydroxystyrene. If a copolymer is made, it may also contain one or more of the following monomers with relatively inert side chains: Styrene, α-methylstyrene, ring-alkylated styrenes such as vinyltoluene, vinylpyridines, vinylimidazole, (meth)acrylic esters such as methyl methacrylate, (meth)acrylic amides such as acrylamide, amides of vinylamine such as N-vinylformamide, vinyl nitriles such as acrylonitrile, vinyl esters such as vinyl acetate, ethylene, propylene, 1-butene, isobutylene, butadiene, isoprene, chloroprene, and vinyl halides such as vinyl chloride.

Further electrophilic scaffolds containing carboxylic acids, sulphonic acids or phosphonic acids, and with a weight average molecular weight of less than 10 kDa, may be formed by radical homopolymerization, random copolymerisation or block copolymerisation of at least one of the monomers (meth)acrylic acid, maleic acid, fumaric acid, crotonic acid, tiglic acid, itaconic acid, S-vinylsulphonic acid, vinylbenzenesulphonic acid, 2-acrylamido-2-methylpropanesulphonic acid (AMPS), 2-sulphoethyl methacrylate, N,N-dimethyl-N-methacryloyloxyethyl-N-(3-sulphopropyl)ammonium betaine (SPE), and P-vinylphosphonic acid. If a copolymer is made, it may also contain one or more of the monomers with relatively inert side chains that were mentioned under "Further nucleophilic scaffolds" above.

Further scaffolds suitable for transesterification and transamidation, and with a weight average molecular weight less than 10 kDa, may be formed by radical homopolymerization, random copolymerisation or block copolymerisation of at least one monomer belonging to the groups of alkyl (meth)acrylates, alkyl crotonates, alkyl tiglates, dialkyl maleate, dialkyl fumarate, and dialkyl itaconate. If a copolymer is made, it may also contain one or more of the following monomers, whose side chains should not affect transesterification or transamidation: Styrene, α-methylstyrene, ring-alkylated styrenes such as vinyltoluene, vinylpyridines, vinylimidazole, (meth)acrylic esters such as methyl methacrylate, (meth)acrylic amides such as acrylamide, amides of vinylamine such as N-vinylformamide, vinyl nitriles such as acrylonitrile, ethylene, propylene, 1-butene, isobutylene, butadiene, isoprene, chloroprene, and vinyl halides such as vinyl chloride.

Further scaffolds containing acylatable, electron-rich aromatic systems with a weight average molecular weight of less than 10 kDa may be formed by radical homopolymerization, random copolymerisation or block copolymerisation of at least one styrene monomer, such as styrene, α-methylstyrene, ring-alkylated styrenes, or 4-hydroxystyrene. If a copolymer is made, it may also contain one or more of the following monomers with non-acylatable side chains: (Meth)acrylic esters such as methyl methacrylate, (meth)acrylic amides such as acrylamide, amides of vinylamine such as N-vinylformamide, vinyl nitriles such as acrylonitrile, vinyl esters such as vinyl acetate, ethylene, propylene, 1-butene, isobutylene, butadiene, isoprene, chloroprene, and vinyl halides such as vinyl chloride.

Further scaffolds containing graftable ether linkages with a weight average molecular weight of less than 10 kDa may be formed by radical homopolymerization, random copolymerisation or block copolymerisation of at least one of the monomers PEG methacrylate, PEG methyl ether methacrylate, PEG ethyl ether methacrylate, PEG methyl ether acrylate, PEG phenyl ether acrylate, poly(propylene glycol) methacrylate, poly(propylene glycol) acrylate, and poly(propylene glycol) methyl ether acrylate. If a copolymer is made, it may also contain one or more of the non-graftable monomers styrene, α-methylstyrene, ring-alkylated styrenes such as vinyltoluene, vinylpyridines, vinylimidazole, (meth)acrylic amides such as acrylamide, amides of vinylamine such as N-vinylformamide, vinyl nitriles such as acrylonitrile, ethylene, propylene, 1-butene, isobutylene, butadiene, isoprene, chloroprene, and vinyl halides such as vinyl chloride, (meth)acrylic acid, maleic acid, fumaric acid, crotonic acid, tiglic acid, itaconic acid, S-vinylsulphonic acid, vinylbenzenesulphonic acid, 2-acrylamido-2-methylpropanesulphonic acid (AMPS), 2-sulphoethyl methacrylate, N,N-dimethyl-N-methacryloyloxyethyl-N-(3-sulphopropyl)ammonium betaine (SPE), and P-vinylphosphonic acid.

Photo-Initiators

The main function of the photo-initiator moieties is to ensure good cross-linking of the thermoplastic, hydrophilic coating to itself and to the substrate, in order to obtain good cohesion and adhesion to the substrate. The preferred properties of the photo-initiator(s) are: (i) good overlap between the lamp emission spectrum and the photo-initiator absorption spectrum; (ii) small overlap or no overlap between the photo-initiator absorption spectrum and the intrinsic, combined absorption spectrum of the other components of the coating (i.e. poly(ethylene oxide)); and good compatibility of the photo-initiator moieties including the scaffold to which the moieties are covalently linked with the poly(ethylene oxide)(s) of the coating.

The photo-initiators should efficiently transform light from the UV or visible light source to reactive radicals which can abstract hydrogen atoms and other labile atoms from polymers and hence effect covalent cross-linking. Optionally, amines, thiols and other electron donors may be added. Radical photo-initiators can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation cleavable photo-initiators spontaneously break down to two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photo-initiators. Addition of electron donors is not required but may enhance the overall efficiency of cleavable photo-initiators according to a mechanism similar to that described for the non-cleavable photo-initiators below.

Recently a new class of β-keto ester based photo-initiators has been introduced by M. L Gould, S. Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20 2005, vol. 1, p. 245-51, Vincentz. After base-catalyzed Michael addition of the ester to polyfunctional acrylates a network is formed with a number of quaternary carbon atoms, each with two neighbouring carbonyl groups. Upon UV or visible light excitation these photo-initiators predominantly cleave by a Norrish type I mechanism and cross-link further without any conventional photo-initiator present, and thick layers may be cured. Such self-initiating systems are within the scope of the present invention.

Excited non-cleavable photo-initiators do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones, thioxanthones, xanthones, anthraquinones, fluorenones, dibenzosuberones, benzils, and phenyl ketocoumarins are important examples of non-cleavable photo-initiators. Most amines with a C—H bond in α-position to the nitrogen atom and many thiols will work as electron donors.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photo-initiator; this could make it possible to cure thick layers.

Such maleimide-containing systems are within the scope of the present invention.

A blend of several photo-initiators may exhibit synergistic properties, as is e.g. described by J. P. Fouassier: "Excited-State Reactivity in Radical Polymerisation Photo-initiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photo-initiator to the other in the pairs [4,4'-bis(dimethylamino)benzophenone+benzophenone], [benzophenone+2,4,6-trimethylbenzophenone], [thioxanthone+methylthiophenyl morpholinoalkyl ketone]. However, many other beneficial combinations may be envisaged.

Furthermore, it has recently been found that covalently linked Irgacure 2959 and benzophenone in the molecule 4-(4-benzoylphenoxyethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20 2005, vol. 2, p. 375-81, Vincentz. This shows that different photo-initiators may show significant synergistic effects when they are present in the same oligomer or polymer. Such covalently linked photo-initiators are also applicable within the present invention.

Hence, in one interesting embodiment of the invention, the photo-initiator moieties include at least two different types of photo-initiator moieties. Preferably the absorbance peaks of the different photo-initiators are at different wavelengths, so the total amount of light absorbed by the system increases.

The different photo-initiators may be all cleavable, all non-cleavable, or a mixture of cleavable and non-cleavable.

The preferred cleavable photo-initiators are benzoin ethers (including benzil dialkyl ketals) such as Irgacure 651 (Ciba); phenyl hydroxyalkyl ketones such as Darocur 1173, Irgacure 127, Irgacure 184, and Irgacure 2959 (all from Ciba), and Esacure KIP 150 and Esacure One (both from Lamberti); phenyl aminoalkyl ketones such as Irgacure 369 (Ciba), Irgacure 379 (Ciba), and Chivacure 3690 (from Double Bond Chemical); methylthiophenyl morpholinoalkyl ketones such as Irgacure 907 (Ciba) and Chivacure 3482 (Double bond Chemicals); and mono- or dibenzoylphosphinoxides such as Irgacure 819 and Darocur TPO (both from Ciba).

The preferred non-cleavable photo-initiators are benzophenone, 4-benzoylbenzoic acid (=4-carboxybenzophenone) and esters thereof, 2-benzoylbenzoic acid (=2-carboxybenzophenone) and esters thereof, 4,4'-bis(dimethylamino)benzophenone (Michler's ketone), 2,4,6-trimethylbenzophenone, BTDA, Omnipol BP (IGM Resins), and other benzophenone derivatives; thioxanthones such as Omnipol TX (IGM Resins) and 2-carboxymethoxythioxanthone (Pentagon Fine Chemical); xanthones; anthraquinones; fluorenones; dibenzosuberones; benzils and other α-diketo compounds such as camphorquinone; and phenyl ketocoumarins. The preferred optional electron donors are benzocaine (ethyl 4-aminobenzoate), PVP-DMAEMA, tribenzylamine, triethanolamine, 2-(N,N-dimethylamino)ethanol, and N,N-dimethylethylenediamine.

The currently most preferred photo-initiators are those selected from the group Irgacure 2959, BTDA and derivatives thereof, 4-carboxybenzophenone and derivatives thereof, 2-carboxybenzophenone and derivatives thereof, and 2-carboxymethoxythioxanthone and derivatives thereof.

Modification of Photo-Initiators to be Suitable for Covalent Bonding to a Scaffold Most common photo-initiators, such as benzoin ethers (e.g. Irgacure 651, cleavable), hydroxyalkyl phenyl ketones (e.g. Darocur 1173, cleavable), benzophenones (e.g. benzophenone, non-cleavable), and thioxanthones (e.g. 2-isopropylthioxanthone, non-cleavable), have no functional groups and therefore cannot be easily bonded to the scaffold. For this reason photo-initiators with one or more functional groups are preferred. The number of commercially available photo-initiators with functional groups is limited, perhaps because photo-initiators have traditionally been employed as mono-functional, non-polymerized ingredients in coating compositions. Hence it may be necessary to custom synthesize certain functional photo-initiators in order to be able to bind them to the scaffold.

Whereas a vast number of chemical reactions are known which form covalent bonds between two separate compounds, the present invention focuses on the presence of either a primary hydroxyl or amino group (i.e. a strong nucleophile) or a reactive carboxylic acid derivative, such as an anhydride or an acid chloride (i.e. a strong electrophile), in the photo-initiator. The following examples will illustrate this:

Irgacure 2959 (from Ciba) is a Norrish type I photo-initiator which contains a nucleophilic primary hydroxyl group:

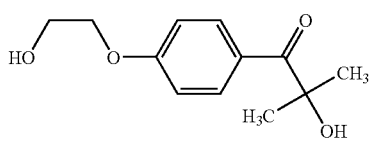

Irgacure 2959

If stronger nucleophilicity is needed, Irgacure 2959 may be sulfonated and then transformed into the corresponding primary amine, e.g. by the Gabriel synthesis (see e.g. J. March: "Advanced Organic Chemistry. Reaction, Mechanisms, and Structure", 3. ed., p. 377-9, Wiley-Interscience, New York, 1985):

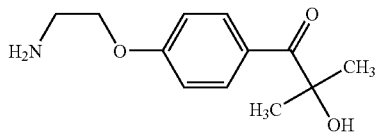

Irgacure 2959 amine

The hydroxyl group in Irgacure 2959 may be functionalized to an electrophilic acid derivative in several ways, so that it may react with free hydroxyl and amino groups:

1. The acid derived from Cr(VI)-oxidation of Irgacure 2959:

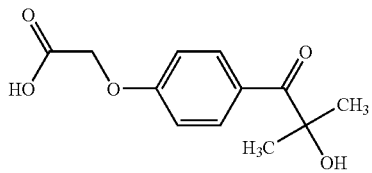

Irgacure 2959 acid

2. The acid derived from 1:1 reaction between Irgacure 2959 and succinic anhydride:

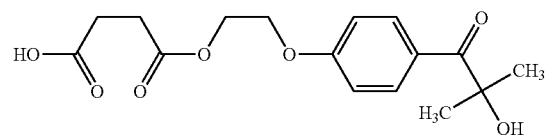

Irgacure 2959-succinic anhydride adduct

3. The acid derived from 1:1 reaction between Irgacure 2959 and maleic anhydride:

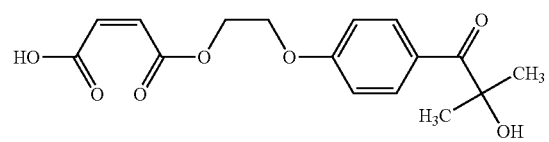

Irgacure 2959-maleic anhydride adduct

These acids may conveniently be turned into the corresponding, reactive acid chlorides by treatment with $SOCl_2$.

Care must be taken to use the acid chlorides soon after formation to avoid reaction between the acid chloride part and the tertiary hydroxyl group in the hydroxyalkyl part of the ketone.

Conversely, electrophilic 2-, 3- or 4-benzoylbenzoyl chloride (formed by reaction between $SOCl_2$ and commercially available 2-, 3- or 4-benzoylbenzoic acid, which are derivatives of the non-cleavable photo-initiator benzophenone) may be transformed into a nucleophile by slow addition to a large excess of ethylene glycol in order to form the corresponding 2-hydroxyethyl benzoylbenzoates, e.g.:

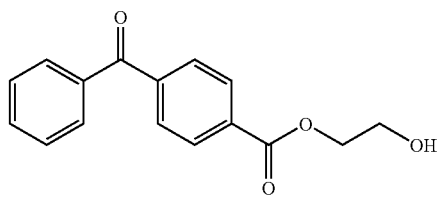

2-Hydroxyethyl 4-benzoylbenzoate

If ethanolamine or ethylenediamine is used instead of ethylene glycol, then the corresponding N-(2-hydroxyethyl)benzoylbenzamides and N-(2-aminoethyl)benzoylbenzamides may be formed. All these nucleophilic derivatives may e.g. react with polyanhydrides such as poly(styrene-co-maleic anhydride) (SMA) (see further below), and with isocyanates. Alternatively, 2-, 3- or 4-hydroxybenzophenone, or 2-, 3- or 4-aminobenzophenone, may be obtained commercially and used directly, although the nucleophilicity of these hydroxyl and amino groups will be considerably smaller than that of the ethylene glycol, ethanolamine and ethylenediamine derivatives mentioned above.

Thioxanthones are also very interesting, non-cleavable photo-initiators because they absorb near 400 nm and hence may be cured by UV-A light or by visible, blue light. An example of a derivative of thioxanthone is 2-carboxymethoxyxanthone, which may be transformed into the electrophilic acid chloride and further, if desired, into nucleophilic species by reaction with excess ethylene glycol (to form 2-hydroxyethyl thioxanthon-2-yloxyacetate), ethanolamine (to form N-(2-hydroxyethyl)thioxanthon-2-yloxyacetamide), or ethylenediamine (to form N-(2-aminoethyl)thioxanthon-2-yloxyacetamide), as described above.

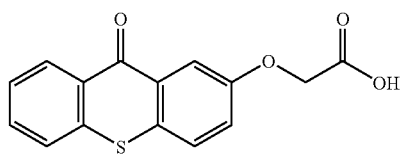 [SMILES: O=C(O)COc1ccc2sc3ccccc3c(=O)c2c1]

Examples of Coupling Between Photo-Initiator Moieties and Scaffolds

Nucleophilic scaffolds, such as Boltorn H20 with 16 free OH groups, may react directly with electrophilic photo-initiators, such as 4-benzoylbenzoyl chloride, to form a photoactive polyester:

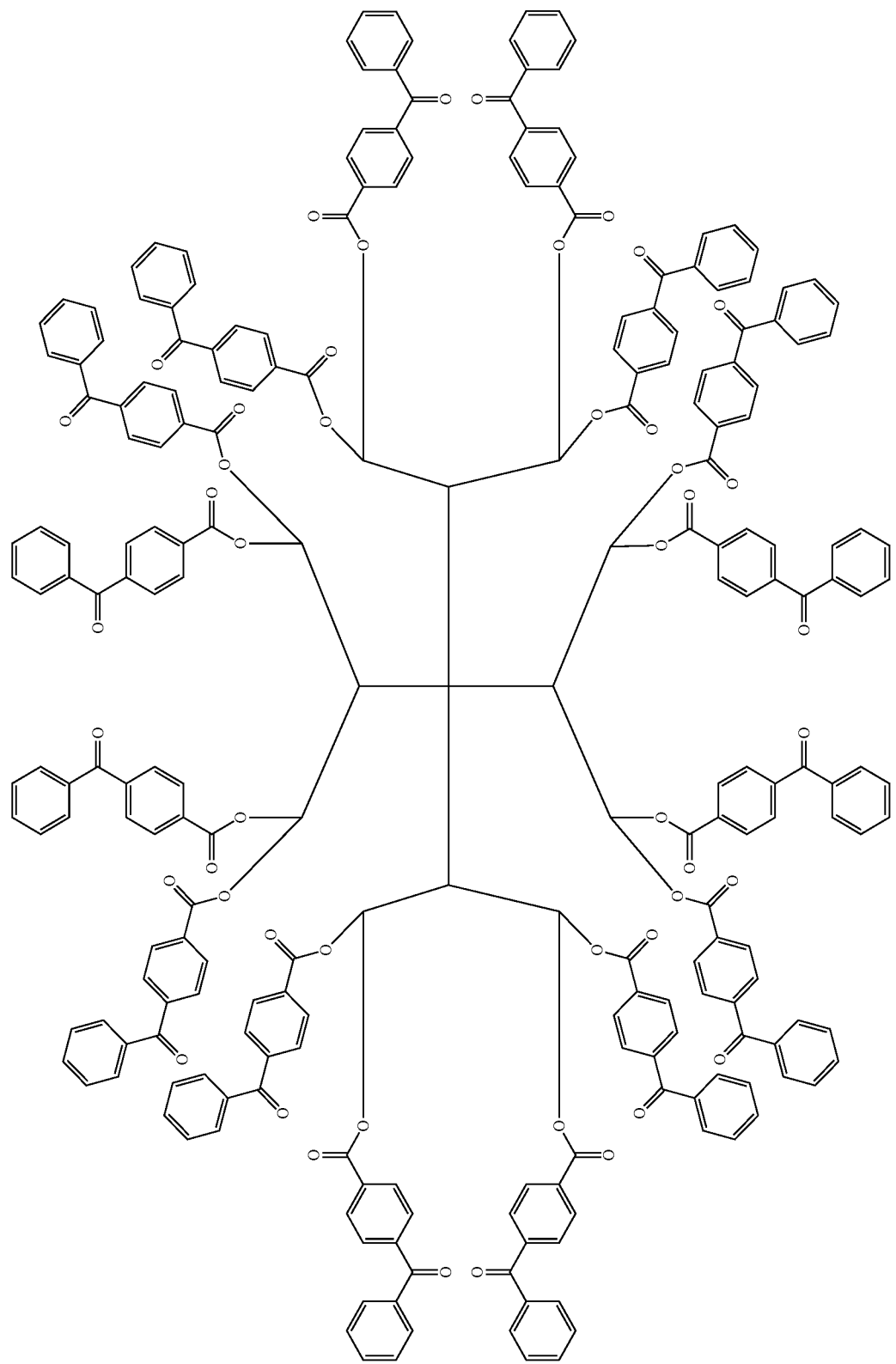

The degree of photo-initiator substitution on the polyol can be controlled if the acid chloride is added to the Boltorn solution.

The acidic components of the electrophilic scaffolds, such as the carboxylic acid groups in poly(acrylic acid), may be transformed to the corresponding acid chlorides, sulphonyl chlorides or phosphonyl chlorides by treatment with $SOCl_2$ or $PCl_5$. Alternatively, the acids may be treated with a dehydrating agent, such as N,N'-dicyclohexylcarbodiimide, to form species resembling acid anhydrides in reactivity towards nucleophiles. Such acid chlorides, sulphonyl chlorides and phosphonyl chlorides and the corresponding anhydrides are activated towards reaction with nucleophilic photo-initiators, such as Irgacure 2959, to form the respective esters, amides, sulphonyl esters, sulphonamides, phosphonyl esters, and phosphonamides:

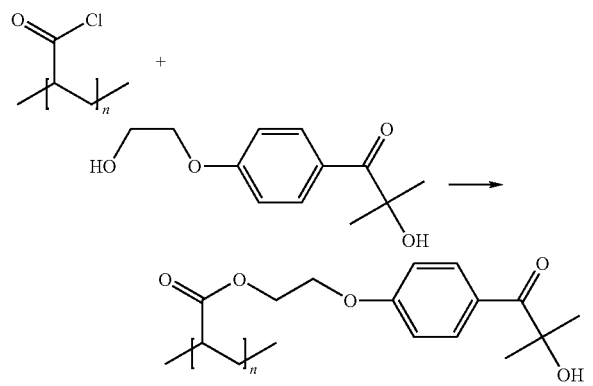

Photoactive esters and amides may be formed with excess photo-active nucleophiles by transesterification or transamidation of esters from the scaffold. Catalysts (such as manganese or zinc salts) may be added, and a vacuum may be applied if the photo-inactive component to be removed has a lower boiling point than the photoactive component, so as to remove the photo-inactive component from the equilibrium. The two reactions may be represented as follows:

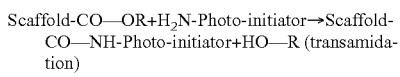

"Scaffold-CO—OR" may be e.g. poly(diethyl maleate) with a weight average molecular weight not exceeding 10 kDa. "HO-Photo-initiator" may be e.g. Irgacure 2959, 2- or 4-hydroxybenzophenone, 2-hydroxyethyl 4-benzoylbenzamide, N-(2-hydroxyethyl)-2-benzoylbenzamide, 2-hydroxyethyl thioxanthon-2-yloxyacetate, or N-(2-hydroxyethyl) thioxanthon-2-yloxyacetamide. "$H_2N$-Photo-initiator" may be e.g. Irgacure 2959 amine, N-(2-aminoethyl)-4-benzoylbenzamide, or N-(2-aminoethyl)thioxanthon-2-yloxyacetamide:

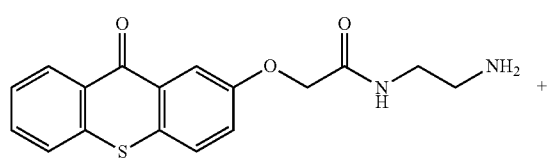

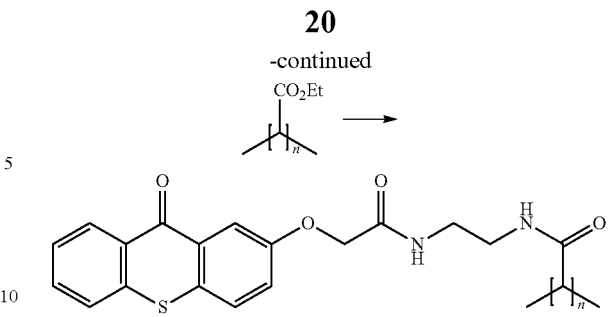

Ethers such as PEG or poly(propylene glycol) may be acyloxylated by reaction with a tert-butyl peroxyester of a carboxyl-containing photo-initiator to give the ether ester and tert-butyl alcohol (see J. March: "Advanced Organic Chemistry. Reaction, Mechanisms, and Structure", 3. ed., p. 636-7, Wiley-Interscience, New York, 1985). As an example, the coupling with a benzophenone derivative (2-benzoylbenzoyl chloride) is shown here:

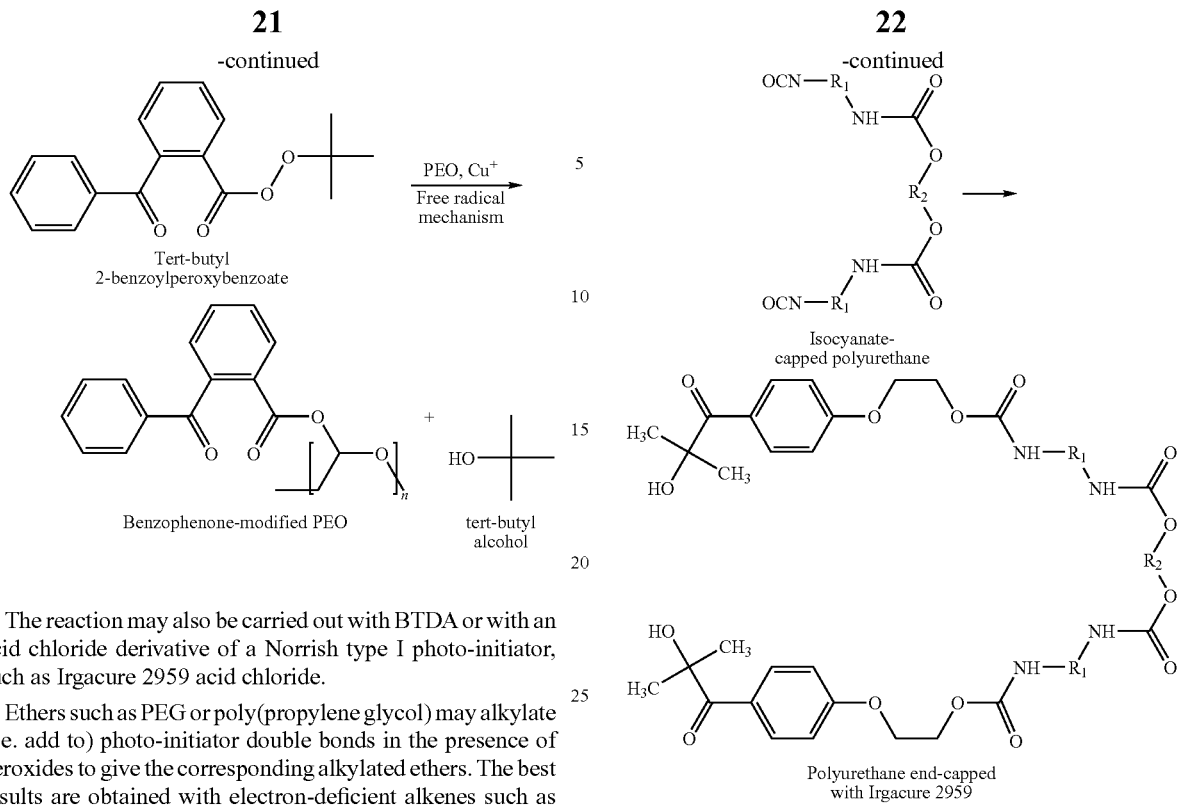

The reaction may also be carried out with BTDA or with an acid chloride derivative of a Norrish type I photo-initiator, such as Irgacure 2959 acid chloride.

Ethers such as PEG or poly(propylene glycol) may alkylate (i.e. add to) photo-initiator double bonds in the presence of peroxides to give the corresponding alkylated ethers. The best results are obtained with electron-deficient alkenes such as maleic anhydride (see C. Walling, E. S. Huyser (1963): "Free radical additions to olefins to form carbon-carbon bonds", Organic Reactions, 13, 91-149). A nucleophilic photo-initiator (such as Irgacure 2959) may e.g. acquire an electron-deficient double bond by esterification with maleic anhydride.

Similarly, the side chains of the scaffold poly(styrene-co-maleic anhydride) (SMA) may be modified with a nucleophilic photo-initiator (such as Irgacure 2959 or modified benzophenones):

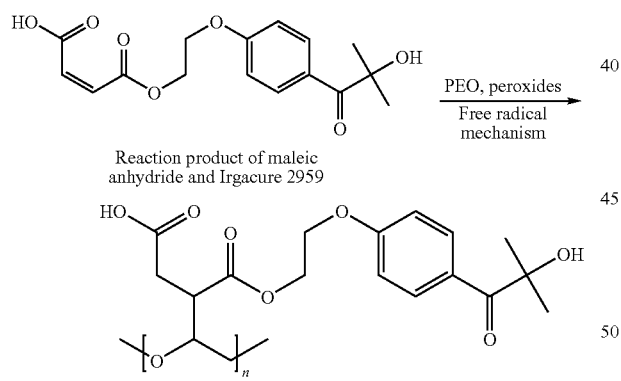

Isocyanate-capped, low-molecular HPEU as the scaffold may also be functionalized with a nucleophilic photo-initiator (such as Irgacure 2959) at both ends to form a photo-active polyurethane:

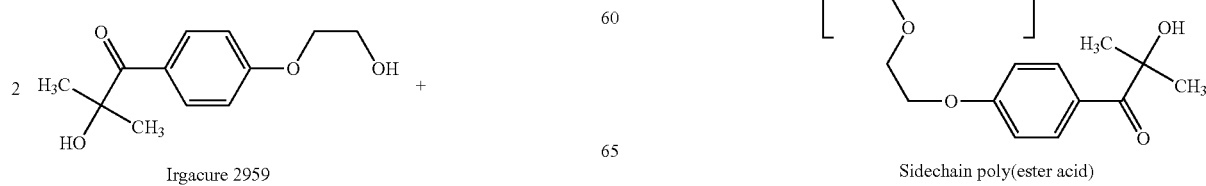

Examples of Transformation of a Scaffold to a Photo-Initiator

Benzophenones may be formed in situ by Friedel-Crafts benzoylation of an electron-rich aromatic moiety with benzoyl chloride and a Lewis acid as catalyst, e.g. AlCl$_3$. Aromatic anhydrides, such as phthalic anhydride, pyromellitic dianhydride (1,2,4,5-benzenetetracarboxylic acid dianhydride) and BTDA, are less reactive than benzoyl chloride but may also be used. If the para position of the aromatic moiety is vacant, then the para compound is the main product because of the size of the benzoyl group (see e.g. J. March: "Advanced Organic Chemistry. Reaction, Mechanisms, and Structure", 3. ed., p. 484-7, Wiley-Interscience, New York, 1985). However, the method may also be used with aromatic moieties which do not have a vacant para position. The aromatic moiety may be part of homo- or copolymers of vinylpyridine, styrene, α-methylstyrene, vinyltoluene, alkoxystyrene, aryloxystyrene, ethylstyrene, tert-butylstyrene, isopropylstyrene, dimethylstyrene, and other alkylated styrenes. Any aromatic diisocyanates or aromatic diols that have been employed in the production of HPEU may also be benzoylated. The aromatic ring of the benzoyl chloride may also itself be substituted; electron donating substituents on the benzoyl chloride will increase the rate of reaction. As an example, with ordinary polystyrene the following reaction occurs:

Correspondingly, α,α-dialkyl-α-hydroxy substituted acetophenones (i.e. cleavable photo-initiators) may also be formed in situ by Friedel-Crafts acylation of an electron-rich aromatic moiety with the relevant α,α-dialkyl-α-hydroxy-acetylchloride. For example, to make a 2-hydroxy-2-propyl phenyl ketone, the electron-rich aromatic moiety must be treated with 2-hydroxy-2-methylpropionyl chloride (=2-hydroxyisobutyryl chloride=α-hydroxyisobutyryl chloride). The precursor of this acid chloride, α-hydroxyisobutyric acid, is e.g. available from Sigma-Aldrich.

Care must be taken that the acid chloride, once formed, does not react with the tertiary hydroxyl group to form the polyester poly(2-isobutyrate).

Examples of Synthesis of a Scaffold with Photo-Initiator Incorporated in the Backbone A difunctional, electrophilic photo-initiator, such as BTDA, may react with a dihydroxy- or diamino-terminated, nucleophilic scaffold fragment, e.g. a low-molecular HPEU, to form the corresponding photo-initiator-containing scaffold:

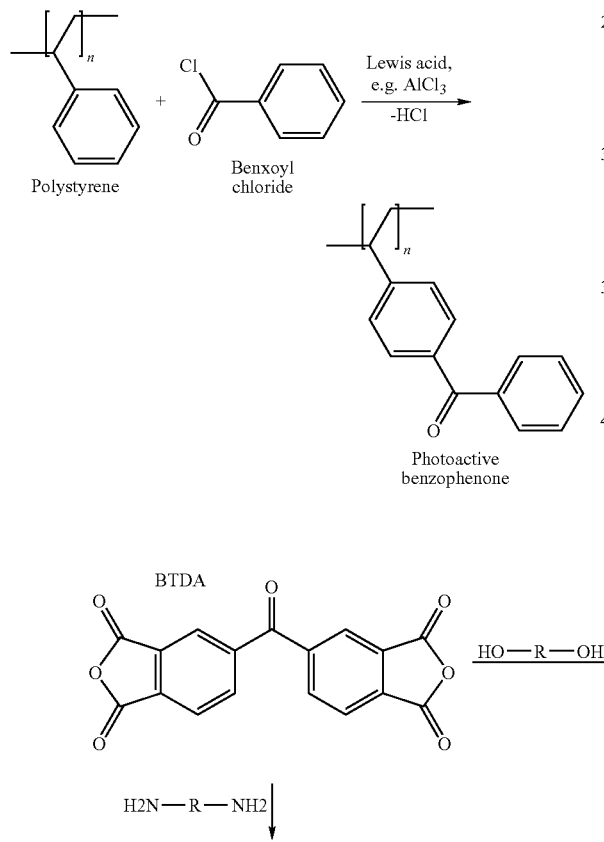

The resulting scaffolds have photo-initiating moieties in the backbone instead of in the side chains. Such scaffolds are within the scope of the present invention. The reactions run best in polar organic solvents such as DMSO, DMA, DMF, NMP, and pyridine.

The cross-linking reaction of the photoactive BTDA-based poly(ester urethane acid) will be:

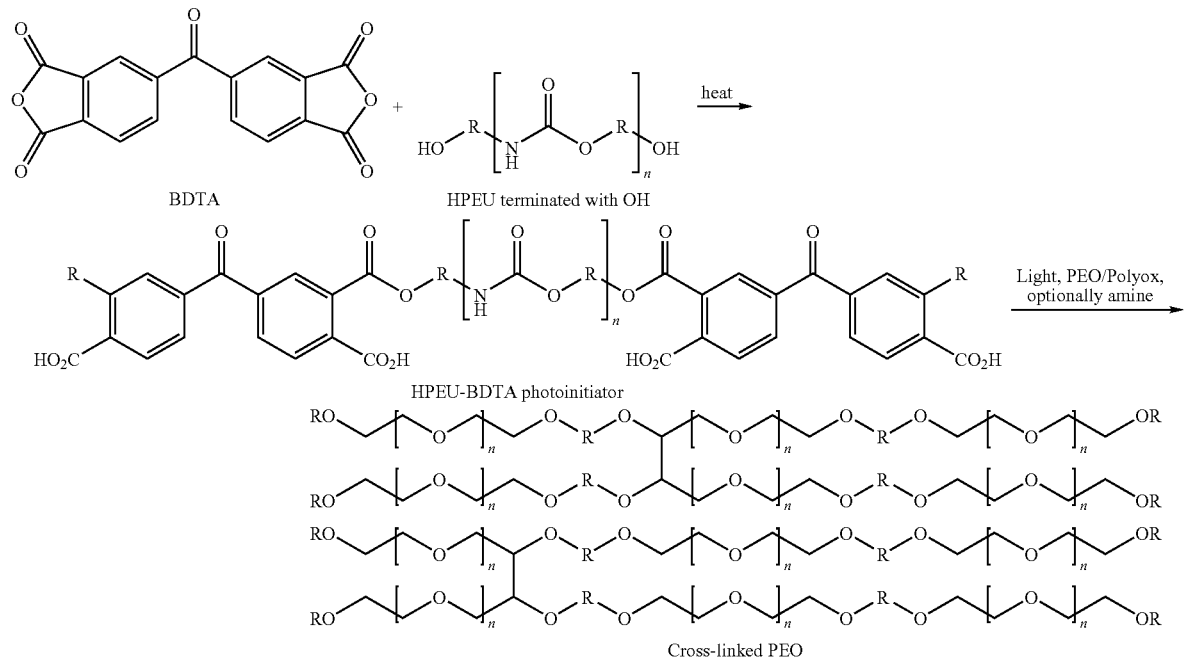

Jeffamine D-230 (from Huntsman; hydrophobic; a=2-3, b=c=0), which is shown below, also reacts willingly with BTDA:

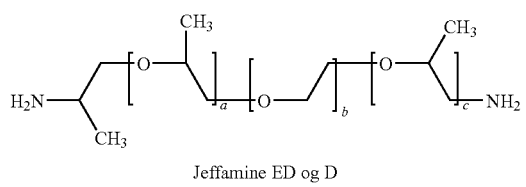

Jeffamine ED og D

As mentioned above, BTDA may also react with the hydroxyl end groups of low molecular weight scaffold fragments, such as low-molecular PEG and other low molecular weight polyethers. Upon photo-curing of PEO with a BTDA-containing scaffold a stable, cross-linked, hydrophilic polymer network is formed, which becomes very slippery when wet.

Detailed Procedure for the Preparation of a Medical Device Element

Step (i)

In an initial step of the method, the prefabricated shaped article and/or the thermoplastic substrate polymer are provided.

As it is clear from the section "Thermoplastic substrate polymer", the substrate polymer is typically a commercial product traded in a suitable physical form, e.g. as pellets, chips, granules, etc. Hence, pre-treatment or preparation is normally not necessary.

If a mixture of two or more substrate polymers is used, it is typically desirable to homogenize the polymers, either in a melted form or by dissolving the polymers in a common solvent followed by solvent removal by conventional procedures and involving conventional equipment, such as spray coating, roller drying or precipitation in a non-solvent. Preferably, the solvent solution is cast into a film and the solvent removed from the film by any conventional technique. Reduced pressure and/or elevated temperature may be used to aid solvent removal. The resulting homogeneous blend may be chipped or pelletized prior to melt processing.

It is further clear from the section "Prefabricated shaped article" that the shaped article is often available from commercial sources, or is readily prepared as will be known by the skilled person within the relevant art. Alternatively, but also very interestingly, the shaped article may be prepared immediately prior to its use in the method of the invention, in certain embodiments even in the same process line as the one where the method is applied. Moreover, the prefabricated shaped article may be pre-treated and even pre-coated prior to use in the method of the invention.

Step (ii)

The coating composition for the preparation of the medical device element may be prepared by dissolving the constituents thereof in a common solvent. The solvent may then be removed to leave a homogeneous blend of the poly(ethylene oxide)(s), any non-thermoplastic hydrophilic polymers and the scaffold(s) having photo-initiator moieties, as well as any additives, which is ready for extrusion. Any conventional procedure or equipment may be used for solvent removal, such as spray coating, roller drying or precipitation in a non-solvent such as acetone or carbon tetrachloride. Preferably the solvent solution is cast into a film and the solvent removed from the film by any conventional technique. The cast film may then be heated in a convection oven at a temperature from ambient to about 70° C. Reduced pressure may be used to aid solvent removal. The resulting homogeneous blend may be chipped or pelletized prior to melt processing or powder coating.

This pelletized coating composition may subsequently be extruded, injection moulded or powder coated on the prefabricated shaped article or the thermoplastic substrate polymer as described for step (iii) below.

Step (iii)

This step involves extruding, injection moulding or powder coating the coating composition of step (ii) on the prefabricated shaped article or together with the thermoplastic substrate polymer of step (i) so as to provide the medical device element of said prefabricated shaped article and/or substrate polymer having thereon a layer of said coating composition, wherein, when both of said prefabricated shaped article and substrate polymer are present, said prefabricated shaped article has thereon a layer of said substrate polymer.

Three main embodiments are encompassed by this step.

In a first main embodiment, only a prefabricated shaped article is provided in step (i), and step (iii) involves extruding, injection moulding or powder coating the coating composition of step (ii) on the prefabricated shaped article of step (i) so as to provide the medical device element of said prefabricated shaped article having thereon a layer of said coating composition.

In a second main embodiment, only a thermoplastic substrate polymer is provided in step (i), and step (iii) involves extruding or injection moulding the coating composition of step (ii) together with the thermoplastic substrate polymer of step (i) so as to provide the medical device element of said thermoplastic substrate polymer having thereon a layer of said coating composition.

In a third main embodiment, a prefabricated shaped article as well as a thermoplastic substrate polymer are provided in step (i), wherein step (iii) involves extruding or injection moulding the coating composition of step (ii) on the prefabricated shaped article together with the thermoplastic substrate polymer of step (i) so as to provide the medical device element of said prefabricated shaped article and said thermoplastic substrate polymer, said prefabricated shaped article having thereon a layer of said thermoplastic substrate polymer and said thermoplastic substrate polymer having thereon a layer of said coating composition.

The three main embodiments will be discussed in the following.

In a first variant of the first main embodiment, a melt of the coating composition is extruded onto a surface of a prefabricated shaped article (see, e.g., Example 6).

In a second variant of the first main embodiment, a melt of the coating composition is injection moulded onto a surface of a prefabricated shaped article.

In a third variant of the first main embodiment, the coating composition is powder coated onto a surface of a prefabricated shaped article.

In one variant of the second main embodiment, a melt of the thermoplastic substrate polymer and a melt of the coating composition are extruded to give a shaped article having a coating of the coating composition on the surface of the substrate polymer.

In another variant of the second main embodiment, a melt of the thermoplastic substrate polymer and a melt of the coating composition are injection moulded to give a shaped article having a coating of the coating composition on the surface of the substrate polymer. This interesting variant can be accomplished in a two step injection moulding process wherein in the outer layer of the coating composition is first moulded followed by the moulding of the thermoplastic substrate polymer.

In one variant of the third main embodiment, a melt of the substrate polymer and a melt of the coating composition are extruded onto a surface of a prefabricated shaped article.

In another variant of the third main embodiment, a melt of the substrate polymer and a melt of the coating composition are injection moulded onto a surface of a prefabricated shaped article. This interesting variant can be accomplished in a two step injection moulding process wherein in the outer layer of the coating composition is first moulded using a solid core followed by the moulding of the thermoplastic substrate polymer using the prefabricated shaped article as the core.

The coating composition may be extruded/co-extruded with the substrate polymer using any conventional and commercially available extrusion equipment. Suitable co-extrusion apparatus may be purchased, for example, from Genca Cable Company, Clearwater, Fla., or from Wayne Machine and Die Company, Totowa, N.J., or, if desired, custom co-extrusion apparatus can be designed for fabrication of any specific medical device element.

Alternatively, the composition may be crosshead-extruded or co-extruded onto a prefabricated shape article, e.g. polymeric article. Extrusion of a skin layer is a conventional process in which a melt of a thermoplastic material (here the thermoplastic substrate polymer or the coating composition) is metered through a die directly onto a solid, continuous, shaped surface.

Moreover, (co)extrusion and injection moulding may be conducted as described in U.S. Pat. Nos. 5,061,424 and 6,447,835.

The coating composition may also injection moulded so as to provide a coating on a thermoplastic substrate polymer or prefabricated shaped article. The injection moulding variants may one or two process steps. In one variant corresponding to the second variant of the first main embodiment (see above), the coating composition is injected at high pressure into a mould, which is the inverse of the shape of the final product, using a solid core of the prefabricated shaped article. In a second variant (corresponding to the second variant of the second main embodiment (see above), step (iii) can be accomplished in two sub-steps, namely by first moulding the coating composition using a solid core, removing the solid core, and subsequently moulding the thermoplastic substrate polymer, optionally using a slightly smaller solid core. In a third variant (corresponding to the second variant of the third main embodiment (see above), step (iii) can be accomplished in two sub-steps, namely by first moulding the coating composition using a solid core, removing the solid core, and subsequently moulding the thermoplastic substrate polymer, using the prefabricated solid article as the solid core. In a fourth variant (corresponding to the second variant of the second main embodiment (see above), step (iii) can be accomplished in two sub-steps, namely by first moulding the thermoplastic substrate polymer using a cavity of one size, removing the cavity, and subsequently moulding the coating composition onto the thermoplastic substrate polymer using a slightly larger cavity. In a fifth variant (corresponding to the second variant of the third main embodiment (see above), can be accomplished in two sub-steps, namely by first moulding the thermoplastic substrate polymer using a cavity of one size and the prefabricated shaped article as the core, removing the cavity, and subsequently moulding the coating composition onto the thermoplastic substrate polymer using a slightly larger cavity.

With regard to powder coating which generally follows conventional principles, the pelletized compound containing poly(ethylene oxide)(s), any non-thermoplastic hydrophilic polymers and scaffold(s) having photo-initiator moieties can be milled to a particle size in the range of 5 to 250 micrometers. Usually a powder coating composition with a particle size distribution in the range of 10 to 100 micrometers is preferred.

The powder coating compositions are typically applied by spraying or by the use of a fluidized bed system. In case of a metal substrate (prefabricated shaped article), application of the coating by electrostatic spraying is preferred. In case of spraying the powder coating can be applied in a single sweep or in several passes to provide a film having the preferred thickness.

After applying the powder by spraying or by using a fluidized bed system or any other powder coating application technology known in the industry, the thermoplastic powder is heated to about 80 to 200° C., depending on the type of substrate, to form a uniform coating layer about 5 to 250 micrometers thick, usually about 10 to 100 micrometers thick.

The thickness of the dry layer of the coating composition is typically 2.5-500 µm, preferably 2.5-125 µm.

The thickness of the substrate polymer (if present) is typically 5-1000 µm, more typically 10-50 µm or 100-500 µm.

The medical device element obtained by the method is dry and in general non-sticky until humidified by finger-touch or wetted with a liquid, at which time it develops a slippery, lubricious surface.

The method of the invention is particularly useful for the preparation of medical device elements having the shape of a rod or tubing. For example, a catheter thus prepared becomes instantly lubricious when it comes into contact with a water-containing fluid and thereby contributes greatly to the comfort of a patient undergoing catheterization. An extruded rod in the form of a guide-wire becomes lubricious when wet and thus slides easily.

After extrusion or injection moulding, it may be necessary to cool the medical device element, e.g. by cold air or in a water bath.

This being said, the currently most preferred embodiments of the step (iii) are those involving (co)extrusion.

Step (iv)

In a subsequent step, the coating composition is irradiated with UV or visible light so as to covalently cross-link the coating composition. UV or visible light is defined as light having a wavelength of 100-750 nm. Particularly relevant wavelength ranges are 100-250 nm and 250-400 nm (both UV light), and 400-750 nm (visible light). In the present context, the terms "photo-curing", "photo-cure" and the like refer to curing by means of UV or visible light. Curing by means of UV light is preferred, although curing by means of blue light (visible light wavelength range) is equally applicable.

The UV or visible light may be applied by means of a polychromatic or monochromatic UV or visible light source, preferably with high intensity and with an emission spectrum that matches the absorbance spectrum of the photo-initiator(s) as well as possible. In the absence of reactive monomers, the cross-linking of the coating takes place only by the bimolecular combination of radicals derived from the UV (or visible light) irradiated photo-initiators. Hence, if the light intensity is doubled, the concentration of radicals is also doubled, but the amount of cross-linking reactions is quadrupled. This is why a high light intensity is preferred. Suitable polychromatic light sources include: (i) deuterium lamps, (ii) mercury lamps, possibly doped with iron, gallium or other elements that significantly affects the output spectrum, (iii) xenon arc lamps, both pulsed and unpulsed, and (iv) halogen lamps (emit mainly visible light). Suitable monochromatic light sources include: (v) gas and solid state lasers (possibly frequency doubled, tripled, quadrupled or in other ways frequency manipulated), both pulsed and unpulsed, and (vi) light emitting diodes in the UV and visible area, both pulsed and unpulsed.

An optimal irradiation period and light intensity can easily be found by the skilled person by routine experiments. For practical reasons (e.g. in the large scale production of the medical device), the irradiation period should preferably not exceed 300 sec, and in particular should not exceed 600 sec.

Currently most preferred embodiments of the method of the present invention include:

I. A method for the preparation of a medical device element, said method comprising the steps of:
(i) providing a thermoplastic substrate polymer;
(ii) providing the coating composition;
(iii) co-extruding the coating composition of step (ii) and the thermoplastic substrate polymer of step (i) so as to provide the medical device element of said substrate polymer having thereon a layer of said coating composition;
(iv) irradiating the coating composition with UV or visible light so as to covalently cross-link said coating composition.

II. A method for the preparation of a medical device element, said method comprising the steps of:
(i) providing a prefabricated shaped article and optionally a thermoplastic substrate polymer;
(ii) providing a coating composition;
(iii) co-extruding the coating composition of step (ii) on the prefabricated shaped article and, if present, the thermoplastic substrate polymer of step (i) so as to provide the medical device element of said prefabricated shaped article and, if present, said substrate polymer having thereon a layer of said coating composition, wherein, when said substrate polymer is present, said prefabricated shaped article has thereon a layer of said substrate polymer;
(iv) irradiating the coating composition with UV or visible light so as to covalently cross-link said coating composition.

III. A method for the preparation of a medical device element, said method comprising the steps of:
(i) providing a thermoplastic substrate polymer;
(ii) providing a coating composition;
(iii) injection moulding the coating composition of step (ii) and the thermoplastic substrate polymer of step (i) so as to provide the medical device element of said substrate polymer having thereon a layer of said coating composition;
(iv) irradiating the coating composition with UV or visible light so as to covalently cross-link said coating composition.

IV. A method for the preparation of a medical device element, said method comprising the steps of:
(i) providing a prefabricated shaped article and optionally a thermoplastic substrate polymer;
(ii) providing a coating composition;
(iii) injection moulding the coating composition of step (ii) on the prefabricated shaped article and, if present, the thermoplastic substrate polymer of step (i) so as to provide the medical device element of said prefabricated shaped article and, if present, said substrate polymer having thereon a layer of said coating composition, wherein, when said substrate polymer is present, said prefabricated shaped article has thereon a layer of said substrate polymer;
(iv) irradiating the coating composition with UV or visible light so as to covalently cross-link said coating composition.

Novel Medical Devices

It is believed that the medical device elements resulting from the method described above represent products which are novel per se. Such medical devices are i.a. characterised by the residues of photo-initiator moieties, and such residues constitute 0.01-20% by weight of the combined amount of the one or more poly(ethylene oxide)s, any non-thermoplastic hydrophilic polymers and the one or more low molecular weight scaffolds.

When used herein, the term "residues of photo-initiator moieties" means the photo-initiator moieties in the form existing after the photo-initiator moieties have conducted the desired action, i.e. to facilitate—either directly or indirectly—the cross-linking of the coating composition, in particular the cross-linking of the chains of the poly(ethylene oxide)(s) and any non-thermoplastic hydrophilic polymers. The residues of the photo-initiator moieties are typically recognized as forms which are rearranged or cleaved ad the molecular level compared to the native photo-initiator.

The content of residues of photo-initiator moieties in the coating can likely be determined from NMR (solution or solid state) spectroscopy as the photo-initiator gives rise to resonances in the aromatic region of the spectrum whereas PEO has resonances in the aliphatic region. Integrated intensities obtained from e.g. a $^1$H-NMR spectrum can be used to determine the content of the photo-initiator relative to other species in the coating. Alternatively, from the elemental analysis and/or XPS analysis a sum-formula of the coating can be deduced, which can directly be used to determine the content of the photo-initiator in the coating. Yet another method is to use the intensity of distinct bands in UV-vis, IR and/or NIR spectra of both the photo-initiator and the other species and entities in the coating. By evaluating the relative intensities the photo-initiator content can be determined. Chromatography techniques such as HPLC, SEC and LC-MS$^n$ may also be used to determine the content of photo-initiator present in a coating by comparing integrated intensities from the chromatograms. In LC-MS$^n$, mass-spectrometry is used to identify the origin of the signals (e.g. from the photo-initiator) in the chromatogram. In for example SEC additional experiments such as NMR is needed to further identify the origin of each signal observed in the chromatogram. In addition, GC-MS techniques may be used similar to LC-MS techniques but with additional needed standards and calibrations prior to analyzing the actual coating composition. Chemical derivatization of the photo-initiator and/or other species and entities in the coating prior to utilizing the analytical techniques described above may be necessary. Atomic absorption measurements also provide an analytical tool for determining the composition of a coating. In principle any spectroscopic and/or spectrometric technique, where distinct integrated signals can be assigned to a specific chemical functionality and relative abundance can be used to determine the relative amount of photo-initiator present in the coating. Prior to determining the relative amount of photo-initiator in a coating some experiments should be performed summarized in the following:

1. Degradation of the photo-initiator should be documented both as a result of heat and UV-vis radiation and possibly relevant combinations thereof. Such degradation information may be used to determine the amount of photo-initiator present in the coating prior to exposing the coating to curing.
2. Diffusion of the photo-initiator present in the coating into a surrounding medium. More specifically, diffusion into an aqueous or highly polar medium as a function of time of one or more photo-initiators present in a coating should be documented. Additionally, diffusion into non-polar media should be documented. Given a hydrophilic coating contained in a medium and the amount of time the coating has been contained, such diffusion data may be used to determine the amount of photo-initiator present in the coating prior to containment.

By having such degradation and diffusion data at hand, it is possible to determine the relative amount of residues of photo-initiator moieties present in a coating prior to processing conditions.

Hence, the present invention also relates to novel medical devices comprising a medical device element of a thermoplastic substrate polymer having thereon a layer of a covalently cross-linked coating composition of (a) as the only polymer constituent(s), one or more poly(ethylene oxide)s optionally in combination with one or more non-thermoplastic hydrophilic polymers, said one or more poly(ethylene oxide)s constituting at least 50% by weight of said polymer constituent(s), and (b) one or more low molecular weight scaffolds having a plurality of residues of photo-initiator moieties, wherein the residues of photo-initiator moieties constitute 0.01-20% by weight of the combined amount of the one or more poly(ethylene oxide)s, any non-thermoplastic hydrophilic polymers and the one or more low molecular weight scaffolds; wherein said coating composition is (co)extruded or injection moulded with said thermoplastic substrate polymer; and wherein the covalent cross-linking of the coating composition is the result of the presence of one or more photo-initiators in the coating composition, said photo-initiator moieties being covalently linked to the low molecular weight scaffold and/or being covalently incorporated into the backbone of the low molecular weight scaffold, and the exposure of the coating composition to UV or visible light.

The present invention further relates to novel medical devices comprising a medical device element of a prefabricated shaped article having thereon a layer of a covalently cross-linked coating composition of (a) as the only polymer constituent(s), one or more poly(ethylene oxide)s optionally in combination with one or more non-thermoplastic hydrophilic polymers, said one or more poly(ethylene oxide)s constituting at least 50% by weight of said polymer constituent(s), and (b) one or more low molecular weight scaffolds having a plurality of residues of photo-initiator moieties, wherein the residues of photo-initiator moieties constitute 0.01-20% by weight of the combined amount of the one or more poly(ethylene oxide)s, any non-thermoplastic hydrophilic polymers and the one or more low molecular weight scaffolds; wherein said coating composition is extruded or injection moulded with said prefabricated shaped article; and wherein the covalent cross-linking of the coating composition is the result of one or more photo-initiators in the coating composition, said photo-initiator moieties being covalently linked to the low molecular weight scaffold and/or being covalently incorporated into the backbone of the low molecular weight scaffold, and the exposure of the coating composition to UV or visible light.

The present invention still further relates to novel medical devices comprising a medical device element of a prefabricated shaped article having thereon a layer of a thermoplastic substrate polymer, where said thermoplastic substrate polymer has thereon a layer of a covalently cross-linked coating composition of (a) as the only polymer constituent(s), one or more poly(ethylene oxide)s optionally in combination with one or more non-thermoplastic hydrophilic polymers, said one or more poly(ethylene oxide)s constituting at least 50% by weight of said polymer constituent(s), and (b) one or more low molecular weight scaffolds having a plurality of residues of photo-initiator moieties, wherein the residues of photo-initiator moieties constitute 0.01-20% by weight of the combined amount of the one or more poly(ethylene oxide)s, any non-thermoplastic hydrophilic polymers and the one or more low molecular weight scaffolds; wherein said coating composition is (co)extruded or injection moulded with said prefabricated shaped article and said thermoplastic substrate polymer; and wherein the covalent cross-linking of the coating composition is the result of the presence of one or more photo-initiators in the coating composition, said photo-initiator moieties being covalently linked to the low molecular weight scaffold and/or being covalently incorporated into the backbone of the low molecular weight scaffold, and the exposure of the coating composition to UV or visible light.

Following the discussion further above, the coating composition does not comprise low-molecular weight residues of ethylenically unsaturated monomers.

The materials useful as the prefabricated shaped article, the thermoplastic substrate polymer and as constituents of the coating compositions are as described above for the method of the invention.

Hence, in one embodiment, the thermoplastic substrate polymer is selected from the group consisting of polyurethanes and PVC.

EXAMPLES

Abbreviations

| Trade name/ trivial name/ abbreviation | Chemical name |
|---|---|
| 2-BBCl | 2-Benzoylbenzoyl chloride |
| BTDA | 3,3',4,4'-Benzophenonetetracarboxylic acid dianhydride |
| Chivacure 3482 | 2-Methyl-1-[4-(alkylthio)phenyl]-2-(4-morpholinyl)-1-propanone (alkyl chain not revealed) |
| Chivacure 3690 | 2-Benzyl-2-(dimethylamino)-1-[4-(alkylmethylamino)phenyl]-1-butanone (alkyl chain not revealed) |
| CMC | Carboxymethylcellulose |
| Darocur 1173 | 2-Hydroxy-2-methylpropiophenone; 2-hydroxy-2-propyl phenyl ketone |
| Darocur TPO | Diphenyl(2,4,6-trimethylbenzoyl) phosphine oxide |
| DMAEMA | N,N-Dimethylaminoethyl methacrylate |
| DMF | N,N-Dimethylformamide |
| DMSO | Dimethylsulfoxide |
| EEA | Copoly(ethylene/ethyl acrylate) |
| EMA | Copoly(ethylene/methyl acrylate) |
| EnBA | Copoly(ethylene/n-butyl acrylate) |
| Esacure KIP 150 | Oligo{2-hydroxy-2-methyl-1-[4-(1-methylvinyl)phenyl]propanone} |
| Esacure One | "Difunctional α-hydroxy ketone" (structure not revealed) |
| EVA | Copoly(ethylene/vinyl acetate) |
| EVA g-MAH | Copoly(ethylene/vinyl acetate)-graft-poly(maleic anhydride) |
| EVOH | Copoly(ethylene/vinyl alcohol) |
| GMA | Glycidyl methacrylate (2,3-epoxypropyl methacrylate) |
| HPEU | Hydrophilic polyetherurethane |
| Irgacure 127 | Bis(4-(2-hydroxy-2-propylcarbonyl)phenyl)methane |
| Irgacure 184 | 1-Hydroxy-1-cyclohexyl phenyl ketone |
| Irgacure 2959 | 2-Hydroxy-2-propyl 4-(hydroxyethoxy)phenyl ketone |
| Irgacure 369 | 2-Benzyl-2-(dimethylamino)-1-[4-(4-morpholinyl)phenyl]-1-butanone |
| Irgacure 379 | 2-(4-Methylbenzyl)-2-(dimethylamino)-1-[4-(4-morpholinyl)phenyl]-1-butanone |
| Irgacure 651 | Benzil α,α-dimethyl ketal; α,α-dimethoxy-α-phenylacetophenone; 2,2-dimethoxy-1,2-diphenyl-1-ethanone |
| Irgacure 819 | Phenylbis(2,4,6-trimethylbenzoyl) phosphine oxide |
| Irgacure 907 | 2-Methyl-1-[4-(methylthio)phenyl]-2-(4-morpholinyl)-1-propanone |
| LDPE | Low density polyethylene |
| LLDPE | Linear low density polyethylene |
| MAH | Maleic anhydride |
| MDI | Methylene-4,4'-diphenyldiisocyanate |
| NMP | N-Methylpyrrolidone |
| NVP | N-Vinyl pyrrolidone |
| Omnipol BP | Poly(tetramethylene glycol) 250 diester of 4-benzoylphenoxyacetic acid |
| Omnipol TX | Poly(tetramethylene glycol) 250 diester of 2-thioxanthonyloxyacetic acid |
| PE | Polyethylene |
| PE g-MAH | Polyethylene-graft-poly(maleic anhydride) |
| Pebax | Polyether-block-polyamide |
| PEG | Poly(ethylene glycol) |
| PEO | Poly(ethylene oxide) |
| PMDA | Pyromellitic acid dianhydride; 1,2,4,5-benzenetetracarboxylic acid dianhydride |
| PP | Polypropylene |
| PS | Polystyrene |
| PVC | Poly(vinyl chloride) |
| PVOH | Poly(vinyl alcohol) |
| PVP | Poly(vinyl pyrrolidone) |
| PVP-DMAEMA | Copoly(vinyl pyrrolidone/N,N-dimethylaminoethyl methacrylate) |
| SBS | Polystyrene-block-polybutadiene-block-polystyrene |
| SEBS | Polystyrene-block-poly(ethylene/butylene)-block-polystyrene |
| SEEPS | Polystyrene-block-hydrogenated poly(isoprene/butadiene)-block-polystyrene |

-continued

| Trade name/<br>trivial name/<br>abbreviation | Chemical name |
|---|---|
| SEPS | Polystyrene-block-poly(ethylene/propylene)-block-polystyrene |
| SIS | Polystyrene-block-polyisoprene-block-polystyrene |
| SMA | Poly(styrene-co-maleic anhydride) |
| THF | Tetrahydrofuran |
| VLDPE | Very low density polyethylene |

§ See J. A. Leon, I. V. Khudyakov from Bomar Specialties, USA (2005): "UV-Light Sensitive (LSR) Urethane Acrylate Oligomers", Proceedings from RadTech Europe 05, Barcelona, Spain, Oct. 18-20, 2005, vol. 2, p. 359-64, Vincentz.

Materials

The PEOs Polyox WSR N-80 (MW 200 kDa) and Polyox N-301 (MW 4 MDa) were from Dow. Irgacure 2959 was from Ciba Specialty Chemicals (Basel, Switzerland). 97% BTDA was from Alfa Aesar. 4-Benzoylbenzoic acid, 2-benzoylbenzoic acid and tert-butyl peroxybenzoate were from Aldrich. CuCl was from Fluka.

SMA 1000 (acid no. 465-495 mg KOH/g sample, MW 5500 g/mol), SMA 2000 (acid no. 335-375 mg KOH/g sample, MW 7500 g/mol), and SMA 3000 (acid no. 265-305 mg KOH/g sample, MW 9500 g/mol) were from Atofina. Boltorn H20 ($M_n$=2100 g/mol, polydispersion index (PDI) =1.3), Boltorn H30 ($M_n$=3500 g/mol, PDI=1.5), and Boltorn H40 ($M_n$=5100 g/mol, PDI=1.8) were from Perstorp.

1-Methylimidazole and pyridine were from Merck. Ethyl acetate, 2-propanol and acetone were from Bie & Berntsen (Denmark). DMSO and thionyl chloride were from Aldrich. Benzene was from Fluka. Methyl isobutyl ketone (MIBK) was from Baker. Dichloromethane was from AppliChem. Jeffamine D-230 was from Huntsman.

All percentages and parts given are weight/weight-% unless otherwise stated.

Subjective Evaluation of Adhesion

The friction and the adhesion to the substrate were evaluated subjectively after swelling in water for at least 24 hours. The adhesion between the two layers (coating and substrate) was given a score from 1 to 4:
1. Complete delamination
2. Poor adhesion, a lot of water blisters
3. Good adhesion, few water blisters
4. Very good adhesion, smooth surface Subjective Evaluation of Gel Cohesion The samples were immersed in deionized water for at least 24 hours. The adhesion of the UV cured coatings to the Estane 58212 substrate was scored as described in Example 1. At the same time the cohesion of the gels was scored on a subjective scale from 1 to 6:
1=No cross-linking; coating dissolved
2=Very weak, loose gel which cannot be handled without breaking
3=Somewhat stable gel
4=Rather stable gel
5=Almost stable gel
6=Entirely stable and cohesive gelExample 1: Coatings consisting of SMA-bound Irgacure 2959 and Polyox Synthesis of the Irgacure 2959 Ester of SMA 1000 (Compound 1)

1.124 g SMA 1000 (4.81 mmol anhydride based on an average acid number of 480 mg KOH/g sample) and 1.373 g Irgacure 2959 (6.12 mmol) were dissolved in 12 g acetone. When 0.503 g 1-methylimidazole (6.13 mmol) was added as combined catalyst and base, the solution turned yellow. The mixture was placed in an airtight, pressure-resistant vial at 70° C. The disappearance of anhydride groups was followed between 1770 and 1860 cm$^{-1}$ by FT-IR and indicated that the reaction was essentially complete after 63 hours (data not shown). Upon cooling the solution became unclear, and a little precipitate was observed. The solution was acidified with HCl to pH 1-2, and the SMA 1000 acid ester of Irgacure 2959 was extracted with ethyl acetate. After drying of the ethyl acetate phase and evaporation of the solvent a viscous, yellowish oil remained. The compound was dissolved in methanol, transferred to a tared Petri dish, put into a ventilated heat cupboard and dried at 70° C. for 80 min to a sticky, yellow compound; this was Compound 1. No further work-up was done. The yield was 2.00 g. The maximum theoretical amount of Irgacure 2959 in the polymer was 49 w/w-%. However, the maximum amount of Irgacure 2959 present in the preparation was determined by UV-Vis spectroscopy to be 22 w/w-%, on the assumption that the extinction coefficients of free and bound Irgacure 2959 were identical. This was an upper estimate, because no correction was made for a possible background absorption at the wavelength of maximum absorbance of Irgacure 2959 (274-5 nm in methanol and 1,3-dioxolane).

Preparation of Sample 1A: Irgacure 2959 Bound to SMA 1000 in a Gel Consisting of Polyox 0.91 parts Compound 1, 89.18 parts Polyox N-301, and 9.91 parts Polyox N-80 were compounded in a Brabender mixer at 120° C. for 2 minutes at atmospheric pressure, then for 2 minutes in vacuum. This mixture contained maximum 0.20% Irgacure 2959. The mixture was hot pressed at 100° C. for a minute to form a circular slice with thickness 1 mm. A quarter of the slice was further hot pressed at 100° C. without distance pieces to a slice that was as thin as possible. The thickness was not measured routinely but was between 150 and 200 µm. The thin slice of Mixture 2 was laminated on a sheet of Estane 58212, which had previously been wiped clean with ethanol, at 100° C. and 50 bars for about 30-45 seconds (no distance pieces used). The sample was divided into two sections, that were both heated to 60-80° C. for 5-10 minutes until they were transparent. One sample was then immediately UV cured for 1 minute and the other for 5 minutes at a distance of about 26 cm from a Fusion I600 H-lamp running at 100% intensity. The samples were subjectively evaluated as described at the introduction of the experimental part.

Synthesis of the Irgacure 2959 Ester of SMA 2000 (Compound 2)

1.428 g SMA 2000 (4.52 mmol anhydride based on an average acid number of 355 mg KOH/g sample) and 1.151 g Irgacure 2959 (5.13 mmol) were dissolved in 12 g acetone. When 0.421 g 1-methylimidazole (5.13 mmol) was added, the solution turned yellow. The mixture was placed in an airtight, pressure-resistant vial at 70° C. The disappearance of anhydride groups was followed between 1770 and 1860 cm$^{-1}$ by FT-IR, which indicated that the reaction was 60-65% complete after 63 hours (data not shown). Hence the reaction was slower than with SMA 1000. The solution was acidified with HCl to pH 1-2, and the SMA 2000 acid ester of Irgacure 2959 was filtered off, dissolved in acetone, transferred to a tared Petri dish, put into a ventilated heat cupboard and dried at 70° C. for 170 min to a pale yellow, mainly hard crystalline substance with a few softer areas; this was Compound 2. No further work-up was done. The yield was 1.88 g. The maximum theoretical amount of Irgacure 2959 in the polymer was 41.5 w/w-%. However, the maximum amount of Irgacure 2959 present in the preparation was determined by UV-Vis spectroscopy to be 11 w/w-%.

Preparation of Sample 1B: Irgacure 2959 Bound to SMA 2000 in a Gel Consisting of Polyox 1.12 parts Compound 2, 88.99 parts Polyox N-301, and 9.89 parts Polyox N-80 were compounded in a Brabender mixer at 120° C. for 2 minutes at atmospheric pressure, then for 2 minutes in vacuum. This mixture contained 0.12% Irgacure 2959. The mixture was hot pressed, laminated and UV cured for 1 and 5 minutes, as described for sample 1A. The samples were subjectively evaluated as described for sample 1A Synthesis of the Irgacure 2959 Ester of SMA 3000 (Compound 3)

1.647 g SMA 3000 (4.18 mmol anhydride based on an average acid number of 285 mg KOH/g sample) and 0.991 g Irgacure 2959 (4.42 mmol) were dissolved in 12 g acetone. When 0.363 g 1-methylimidazole (4.42 mmol) was added, the solution turned yellow. The mixture was placed in an airtight, pressure-resistant vial at 70° C. The disappearance of anhydride groups was followed between 1770 and 1860 cm$^{-1}$ by FT-IR, which indicated that the reaction was 60-65% complete after 63 hours (data not shown). Hence the reaction was slower than with SMA 1000 but about as fast as with SMA 2000. The solution was acidified with HCl to pH 1-2, and the SMA 3000 acid ester of Irgacure 2959 was extracted with methyl isobutyl ketone. After drying of the methyl isobutyl ketone phase and evaporation of the solvent a yellow substance remained. The compound was dissolved in acetone, transferred to a tared Petri dish, put into a ventilated heat cupboard and dried at 70° C. overnight to a pale yellow, transparent, brittle glass; this was Compound 3. No further work-up was done. The yield was 2.22 g. The maximum theoretical amount of Irgacure 2959 in the polymer was 36 w/w-%. However, the maximum amount of Irgacure 2959 present in the preparation was determined by UV-Vis spectroscopy to be 25 w/w-%

Preparation of Sample 1C: Irgacure 2959 Bound to SMA 3000 in a Gel Consisting of Polyox 1.33 parts Compound 3, 88.80 parts Polyox N-301, and 9.87 parts Polyox N-80 were compounded in a Brabender mixer at 120° C. for 2 minutes at atmospheric pressure, then for 2 minutes in vacuum. This mixture contained maximum 0.33% Irgacure 2959. The mixture was hot pressed, laminated and UV cured for 1 and 5 minutes, as described for sample 1A. The samples were subjectively evaluated as described for sample 1A.

Results and Discussion for Samples 1A-C

The results are shown here:

| | | 1 min. UV curing | | 5 min. UV curing | |
|---|---|---|---|---|---|
| Sample | SMA type | Gel cohesion (1-6) | Adhesion to substrate (1-4) | Gel cohesion (1-6) | Adhesion to substrate (1-4) |
| 1A | 1000 | 2 | 1 | 4.5 | 1 |
| 1B | 2000 | 1 | 1 | 1 | 1 |
| 1C | 3000 | 4.5 | 1 | 6 | 3 |

Within the samples with a Polyox coating (1A-C) the cohesion of the gels follows the pattern: SMA 3000 (0.33% Irgacure 2959)>SMA 1000 (0.20% Irgacure 2959)>SMA 2000 (0.12% Irgacure 2959). This order follows the concentration of Irgacure 2959 in the samples, whereas the order of the SMA polymers seems to be random. Hence the concentration of Irgacure 2959 must be at least 0.3% in order to achieve a good UV cross-linking of the gels, whereas the effect of the SMA type appears to be smaller.

When sample 1C was UV cured for 5 minutes a superb gel resulted which, in addition, adhered strongly to the substrate. This effect may be due to the still relatively low concentration of Irgacure 2959 in sample 1C, which allows for better through curing, or the effect may be due to an especially good compatibility of the SMA-bound Irgacure 2959 with both substrate and Polyox.

Example 2

Coatings Consisting of Polyox and Irgacure 2959 Bound to Aliphatic, Hydrophobic Polyurethanes Compounds 4 and 5 were custom synthesized by Bomar Specialties Co (Winsted, Conn.) and distributed in Europe by IGM Resins (Waalwijk, the Netherlands). Compound 4 was an aliphatic, trifunctional polyether urethane of medium molecular weight, which was functionalised with Irgacure 2959 at all three ends. The content of Irgacure 2959 in Compound 4 was 33.0 w/w-%, as indicated by Bomar. Compound 5 was an aliphatic, linear polyether urethane of medium molecular weight, which was functionalised with Irgacure 2959 at both ends. The content of Irgacure 2959 in Compound 5 was 15.5 w/w-%, as indicated by Bomar. Neither compound contained any acrylate groups, as determined by FT-IR (data not shown).

Preparation of Sample 2A: 1% Compound 4 in a Gel Consisting of Polyox 1 part Compound 4, 89.1 parts Polyox N-301, and 9.9 parts Polyox N-80 were compounded in a Brabender mixer at 120° C. for 2 minutes at atmospheric pressure, then for 2 minutes in vacuum. This mixture contained 0.33% Irgacure 2959. The mixture was hot pressed, laminated and UV cured for 1 and 5 minutes, as described for sample 1A. The samples were subjectively evaluated as described for sample 1A.

Preparation of Sample 2B: 5% Compound 4 in a Gel Consisting of Polyox 5 parts Compound 4, 85.5 parts Polyox N-301, and 9.5 parts Polyox N-80 were compounded in a Brabender mixer at 120° C. for 2 minutes at atmospheric pressure, then for 2 minutes in vacuum. This mixture contained 1.65% Irgacure 2959. The mixture was hot pressed, laminated and UV cured for 1 and 5 minutes, as described for sample 1A. The samples were subjectively evaluated as described for sample 1A.

Preparation of Sample 2C: 10% Compound 4 in a Gel Consisting of Polyox 10 parts Compound 4, 81 parts Polyox N-301, and 9 parts Polyox N-80 were compounded in a Brabender mixer at 120° C. for 2 minutes at atmospheric pressure, then for 2 minutes in vacuum. This mixture contained 3.30% Irgacure 2959. The mixture was hot pressed, laminated and UV cured for 1 and 5 minutes, as described for sample 1A. The samples were subjectively evaluated as described for sample 1A.

Preparation of Sample 2D: 1% Compound 5 in a Gel Consisting of Polyox 1 part Compound 5, 89.1 parts Polyox N-301, and 9.9 parts Polyox N-80 were compounded in a Brabender mixer at 120°

C. for 2 minutes at atmospheric pressure, then for 2 minutes in vacuum. This mixture contained 0.16% Irgacure 2959. The mixture was hot pressed, laminated and UV cured for 1 and 5 minutes, as described for sample 1A. The samples were subjectively evaluated as described for sample 1A.

Preparation of Sample 2E: 5% Compound 5 in a Gel Consisting of Polyox 5 parts Compound 5, 85.5 parts Polyox N-301, and 9.5 parts Polyox N-80 were compounded in a Brabender mixer at 120° C. for 2 minutes at atmospheric pressure, then for 2 minutes in vacuum. This mixture contained 0.78% Irgacure 2959. The mixture was hot pressed, laminated and UV cured for 1 and 5 minutes, as described for sample 1A. The samples were subjectively evaluated as described for sample 1A.

Preparation of Sample 2F: 10% Compound 5 in a Gel Consisting of Polyox 10 parts Compound 5, 81 parts Polyox N-301, and 9 parts Polyox N-80 were compounded in a Brabender mixer at 120° C. for 2 minutes at atmospheric pressure, then for 2 minutes in vacuum. This mixture contained 1.55% Irgacure 2959. The mixture was hot pressed, laminated and UV cured for 1 and 5 minutes, as described for sample 1A. The samples were subjectively evaluated as described for sample 1A.

Results and Discussion for Samples 2A-F

The results are shown here:

| Sample | % Irgacure 2959 | Compound number | 1 min. UV curing | | 5 min. UV curing | |
|---|---|---|---|---|---|---|
| | | | Gel cohesion (1-6) | Adhesion to substrate (1-4) | Gel cohesion (1-6) | Adhesion to substrate (1-4) |
| 2A | 0.33 | 4 | 4 | 1 | 5 | 3 |
| 2B | 1.65 | 4 | 5 | 1 | 5 | 3 |
| 2C | 3.30 | 4 | 5 | 1 | 5 | 3 |
| 2D | 0.16 | 5 | 2 | 1 | 2 | 1 |
| 2E | 0.78 | 5 | 5 | 1 | 5 | 1 |
| 2F | 1.55 | 5 | 5 | 1 | 5 | 1 |

Samples 2A-C produced strong gels that adhered well to the substrate after 5 minutes UV curing. Samples 2E-F also produced strong gels after 5 minutes UV curing, but these gels did not adhere to the substrate. These experiments clearly demonstrated that the geometry of the photoactive polymer was more important for the adhesion to the substrate than the sheer concentration of photo-initiating groups in the gel. That is, the trifunctional photoactive polyurethane Compound 4 adhered strongly to the substrate polymer whereas the difunctional Compound 5 did not. It also appeared that 0.16% Irgacure 2959 in the gel was not enough to induce efficient crosslinking of the gel, even after 5 minutes UV curing (sample 2D), as this result was also found for sample 1B.

Example 3

Coatings Consisting of Polyox with BTDA-Jeffamine Condensation Polymers as Photo-Initiator Synthesis of BTDA-Jeffamine D-230 Condensation Polymer (Compound 6)

1.77 g 97% BTDA (5.33 mmol) was dissolved in 12 g DMSO by magnetic stirring and heating to 60° C. 1.23 g Jeffamine D-230 (5.35 mmol) was added with perceptible heat evolution. FT-IR recorded within minutes after mixing indicated that the reaction between the dianhydride and the diamine was instantaneous.

The solution was acidified with HCl to pH 1-2, and the BTDA-Jeffamine D-230 condensation polymer was extracted with dichloromethane. The dichloromethane phase was dried and the dichloromethane evaporated; this was Compound 6. The compound contained maximum 11.4% BTDA, but this could not be verified by UV-Vis spectroscopy because of a large background absorption at the maximum absorption of BTDA (257 nm in ethanol).

Preparation of Sample 3A: BTDA/Jeffamine D-230 Condensation Polymer as Photo-Initiator in a Gel Consisting of Polyox 1.73 parts Compound 6, 88.44 parts Polyox N-301, and 9.83 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A. The samples contained maximum 0.20% BTDA.

Results and Discussion for Sample 3A

The results are shown here:

| | 1 min. UV curing | | 5 min. UV curing | |
|---|---|---|---|---|
| Sample | Gel cohesion (1-6) | Adhesion to substrate (1-4) | Gel cohesion (1-6) | Adhesion to substrate (1-4) |
| 3A | 3 | 1 | 4 | 1 |

A relatively strong gel was formed from sample 3A after 1 minute UV curing in spite of the low concentration of photo-initiator used, but the gel strength at 5 minutes UV curing was better.

Example 4

Coatings Consisting of Polyox with Benzophenone Bound to Boltorn as Photo-Initiator Synthesis of 4-Benzoylbenzoyl Chloride 5.00 g 4-benzoylbenzoic acid (22.1 mmol), 10.0 mL thionyl chloride (16.31 g, 137 mmol) and one drop of DMF in a 100 mL round-bottom flask was refluxed for 75 minutes in an oil bath kept at 100° C. The stream of gaseous SO$_2$ and HCl, that was formed during the reaction, was directed via rubber tubing and a glass pipette onto the surface of a vigorously stirred 1 M NaOH solution, where most of the gas was absorbed and transformed to sulphite and chloride. Care was taken not to let the tip of the glass pipette touch the surface of the sodium hydroxide solution because of the risk of back suction of sodium hydroxide into the system.

After 75 minutes reflux the oil bath was removed, and the reaction mixture was cooled to room temperature. The condenser was removed and the setup rearranged, so a piece of rubber tubing from the round-bottom flask was directed to the entrance of a membrane pump, and the exit from the membrane pump was directed via rubber tubing and a glass pipette towards the stirred 1 M NaOH solution. The glass pipette should be at a larger distance from the NaOH solution than during the first part of the experiment, because the air flow through the pump was much larger than the spontaneous flow of gaseous SO$_2$ and HCl from the first part of the experiment. Then suction was applied and the unreacted SOCl$_2$ removed, first for 10 minutes at room temperature and later with gentle heating of the reaction mixture in the still warm oil bath for another 10 minutes. The flask with the pale, yellow, solid 4-benzoylbenzoyl chloride was stoppered until it was used in the next step of the synthesis. The membrane pump was flushed free of residual SOCl$_2$ by direct suction of 500 mL of deionized water through the pump and into one of two small holes in the lid of a plastic bucket in a fume hood.

Synthesis of the Boltorn H-20 Ester of 4-Benzoylbenzoic Acid (Compound 7)

2.43 g Boltorn H-20 (22.1 mmol OH based on an average OH-number of 510 mg KOH/g sample) was dissolved in 50 mL pyridine (48.9 g; 0.618 mol) in a 250 mL round-bottom flask with a directly attached distillation head. The mixture was dried by distillation by means of a heating mantle with magnetic stirrer, since water forms a low boiling azeotrope with pyridine (azeotrope bp 93.6° C.; azeotrope contains 75.5 mol-% water). As soon as the water was removed, the distillation temperature increased to the boiling point of pure pyridine, i.e. 115.3° C.; from this point an additional 4-5 mL pyridine/water was collected in a measuring cylinder through a small funnel.

A 100 mL dropping funnel, which had been dried in a heat cupboard at 130° C., was placed on the 100 mL round-bottom flask containing 4-benzoylbenzoyl chloride (see above). The warm, dried solution of Boltorn H-20 was transferred to the dropping funnel, and a nitrogen bubbler was attached to exclude moisture. 10-15 mL of the Boltorn solution was added at such a rate that only a small amount of gaseous HCl was formed above the liquid; this should re-enable magnetic stirring in the flask. The rest of the solution was added at such a rate that the temperature of the outside of the flask did not exceed about 40° C., as judged by the bare hand (no external cooling or heating was applied). The reaction mixture became brown. If necessary, the solution was cooled in an ice bath. Towards the end of Boltorn addition the reaction mixture became thicker because of the precipitation of apparently light brown pyridinium chloride. After about an hour the heat evolution had stopped, and the reaction mixture had reverted to room temperature as a sign that the reaction was complete.

Excess concentrated HCl was added to protonate all pyridine to make it water soluble, and the Boltorn ester was extracted from the aqueous phase into 3×50 mL CH$_2$Cl$_2$. The organic extract was dried overnight with MgSO$_4$ and the CH$_2$Cl$_2$ evaporated. The Boltorn H-20 ester of 4-benzoylbenzoic acid was a light tan, hard solid. This was Compound 7.

Preparation of Sample 4A: Boltorn H-20 Ester of 4-Benzoylbenzoic Acid as Photo-Initiator in a Gel Consisting of Polyox 1.45 parts Compound 7, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A.

Synthesis of the Boltorn H-30 Ester of 4-Benzoylbenzoic Acid (Compound 8)

2.48 g Boltorn H-30 (22.1 mmol OH based on an average OH-number of 500 mg KOH/g sample) was dissolved in 50 mL pyridine (48.9 g; 0.618 mol), dried and made to react with 4-benzoylbenzoyl chloride produced from 5.00 g 4-benzoylbenzoic acid, as described in the synthesis of the Boltorn H-20 ester of 4-benzoylbenzoic acid (Compound 7). The Boltorn H-30 ester of 4-benzoylbenzoic acid was a light tan wax. This was Compound 8.

Preparation of Sample 4B: Boltorn H-30 Ester of 4-Benzoylbenzoic Acid as Photo-Initiator in a Gel Consisting of Polyox 1.46 parts Compound 8, 88.69 parts Polyox N-301, and 9.85 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A.

Synthesis of 2-Benzoylbenzoyl Chloride, Batch #1 (Abbreviated "2-BBCl-1")

The synthesis of 2-BBCl-1 was carried out like the synthesis of 4-benzoylbenzoyl chloride (see above). However, 2-BBCl-1 was a yellow oil and not a solid like 4-benzoylbenzoyl chloride.

Synthesis of the Boltorn H-20 Ester of 2-Benzoylbenzoic Acid (Compound 9)

2.43 g Boltorn H-20 (22.1 mmol OH based on an average OH-number of 510 mg KOH/g sample) was dissolved in 50 mL pyridine (48.9 g; 0.618 mol), dried and made to react with 2-BBCl-1 produced from 5.00 g 2-benzoylbenzoic acid as described above. The Boltorn H-20 ester of 2-benzoylbenzoic acid was a light tan, hard solid. This was Compound 9.

Preparation of Sample 4C: Boltorn H-20 Ester of 2-Benzoylbenzoic Acid as Photo-Initiator in a Gel Consisting of Polyox 1.45 parts Compound 9, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A.

Synthesis of the Boltorn H-30 Ester of 2-Benzoylbenzoic Acid (Compound 10)

2.48 g Boltorn H-30 (22.1 mmol OH based on an average OH-number of 500 mg KOH/g sample) was dissolved in 50 mL pyridine (48.9 g; 0.618 mol), dried and made to react with 2-BBCl-1 produced from 5.00 g 2-benzoylbenzoic acid as described above. The Boltorn H-30 ester of 2-benzoylbenzoic acid was a light tan, hard solid. This was Compound 10.

Preparation of Sample 4D: Boltorn H-30 Ester of 2-Benzoylbenzoic Acid as Photo-Initiator in a Gel Consisting of Polyox 1.46 parts Compound 10, 88.69 parts Polyox N-301, and 9.85 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A.

Preparation of Sample 4E: 2-Benzoylbenzoic Acid not Bound to Boltorn H-20 in a Gel Consisting of Polyox 0.24 parts 2-benzoylbenzoic acid, 1.21 parts Boltorn H-20, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 1A. The samples were subjectively evaluated as described for sample 1A.

Results and Discussion for Samples 4A-E

The results are shown here:

| Sample | Photo-initiator? | PI bound? | Polymer? | 1 min. UV curing | | 5 min. UV curing | |
|---|---|---|---|---|---|---|---|
| | | | | Cohesion (1-6) | Adhesion (1-4) | Cohesion (1-6) | Adhesion (1-4) |
| 4A | 4-BBA | Yes | H-20 | 5.5 | 1 | 5.5 | 3 |
| 4B | 4-BBA | Yes | H-30 | 4 | 1 | 4.5 | 4 |
| 4C | 2-BBA | Yes | H-20 | 6 | 1 | 6 | 1 |
| 4D | 2-BBA | Yes | H-30 | 6 | 1 | 6 | 1 |
| 4E | 2-BBA | No | H-20 | 1 | 1 | 6 | 1 |

4-BBA: 4-Benzoylbenzoic acid. 2-BBA: 2-Benzoylbenzoic acid. PI: Photo-initiator. H-20: Boltorn H-20. H-30: Boltorn H-30.

Comparing the samples 4A-D, which all had bound photo-initiators, it was clear that only 4-BBA (4A-B) could secure good adhesion of the coating to the substrate after 5 minutes UV curing of a Polyox-coating, whereas 2-BBA could not (4C-D). On the other hand 2-BBA formed stronger Polyox gels than 4-BBA. Sample 4E with unbound 2-BBA and H-20 did not form a strong gel after 1 minute UV curing, as opposed to all other photo-initiator combinations in Polyox; apparently H-20 worked best with the photo-initiator bound to it.

Example 5

Preparation of a PEG4000 Scaffold Carrying Photo-Initiator Moieties 4-benzoylbenzoic acid (2.63 g, 11.6 mmol) was added to toluene (100 mL) and the mixture was heated to 45° C. Oxalyl chloride (1.85 g, 14.6 mmol) was added followed by a few drops of DMF and the reaction mixture was stirred overnight at 45° C. After removal of the solvent, the residue was dissolved again in toluene (100 mL), a few lumps of $CaH_2$ were added and the mixture was stirred at RT for 1 hour. The mixture was filtered and the solvent was removed leaving the crude acid chloride, which was immediately dissolved in THF (100 mL). $^tBuOOH$ (2.5 mL, 5.5 M in decane, 14 mmol) and 30% KOH (3 mL, 16 mmol) was added simultaneously and the reaction mixture was stirred overnight at RT. 2M $Na_2CO_3$ (50 mL) was added and the organic phase was separated and dried ($MgSO_4$). Celite was then added and the solvent removed. The residue was placed on a column. Column chromatography using gradient elution with EtOAc and heptane left 1.6 g (46%) of tert-butyl 4-benzoylbenzoperoxoate as a slightly yellow oil; $^1H$-NMR ($CDCl_3$, RT): 8.05 (d, 2H, J=8 Hz), 7.84 (d, 2H, J=8 Hz), 7.79 (d, 2H, J=8 Hz), 7.61 (t, 1H, J=8 Hz), 7.49 (t, 1H, J=8 Hz), 1.43 (s, 9H); $^{13}C$-NMR ($CDCl_3$, RT): 195.6, 163.5, 141.7, 136.7, 133.0, 130.7, 130.0, 129.8, 129.0, 128.4, 84.3, 26.2.

PEG 4000 from Clariant (2 g) was dissolved in benzene (200 mL) and freshly prepared CuCl (5 mg) was added. The solution was heated to reflux at which tert-butyl 4-benzoylbenzoperoxoate (1 g, 3.4 mmol) dissolved in benzene (25 mL) was added drop wise and the reaction mixture was further refluxed for 72 h. During the reaction the color changed from slightly green to blue. After cooling to RT the reaction was quenched with 2 M $Na_2CO_3$ (5 mL) and water was subsequently removed by distillation. The mixture was then filtered and the solution was poured into heptane. After some time an oily substance was formed at the bottom of the beaker and remaining solvents was decanted leaving the benzophenone functionalized PEG; This was compound 11. $^1H$-NMR and UV-vis measurements indicate a loading of benzophenone of ~30 wt %. FT-IR measurements showed bands at 1718 $cm^{-1}$ and 1645 $cm^{-1}$ confirming the presence of two keto-functionalities.

Preparation of Sample 5A: Benzophenone Bound to PEO in a Gel Consisting of Polyox Compound 11 (4 parts), Polyox N-301 (88 parts) and Polyox N-80 (8 parts) were compounded in a Brabender mixer at 120° C. for 10 min at atmospheric pressure. The mixture was then hot pressed at 120° C. Considering the loading of benzophenone on the PEO scaffold this mixture effectively contained ~1 w/w-% photo-initiator. For comparison, Polyox N-301 (89 parts), Polyox N-80 (10 parts), and benzophenone (1 part) were compounded at the same conditions as for the compound containing compound 11. Finally, a compound of Polyox N-301 (90 parts) and Polyox N-80 (10 parts) was made and hot pressed. Films of similar dimensions of all three compounds were UV-irradiated using a UV-lamp from Dr. Hönle GmbH for 1 hour. During curing the temperature of the samples rose to above the melting temperatures for the films. Gel properties of the films were evaluated by placing them in Petri dishes and covering them with water. Visual inspection revealed that whereas the mixture without photo-initiator did not form a gel, swelling of the films with both unbound benzophenone and benzophenone bound to the PEO scaffold resulted in gels of similar strength.

Example 6

PEO 1NF from Sumitomo (150-400 kDa) and Irgacure 2959 Bound to Aliphatic, Hydrophobic Polyurethanes

| Ingredients | Compound A | Compound B | Compound C | Compound D |
|---|---|---|---|---|
| PEO 1NF from Sumitomo | 99.5% | 98.0% | 97.0% | 94.0% |
| Irgacure 2959 bound to aliphatic, hydrophobic polyurethanes (example 2) | 0.5% | 2.0% | 3.0% | 6.0% |

These ingredients were compounded in a twin-screw extruder. The ingredients were fed to the extruder by gravimetric feeders, extruded into strands and pelletized.

The extruder profile was:

|   | zone 1 | zone 2 | zone 3 | zone 4 | zone 5 | zone 6 | zone 7 | zone 8 | zone 9 | Die |
|---|---|---|---|---|---|---|---|---|---|---|
| °C. | 40 | 50 | 60 | 80 | 80 | 80 | 80 | 90 | 90 | 90 |

Two single screw extruders were then connected to a single crosshead dual tube die. Both extruder #1 and extruder #2 were charged with Compound A. The blends were extruded onto a prefabricated tube of Estane 58212 to form a monolayer with a speed at 15 m/min. The same procedure was repeated with Compound B, C and D and thin monolayers were formed and UV cured inline with a Fusion 600I H-lamp at 80 and 100% intensity.

The ratios of inner to outer layer was varied by adjusting the output of either extruder by increasing or lowering the screw speed. The thickness of the layers was adjusted by varying either the output or the haul-off speed.

The two extruders had the same temperature profile.

|   | zone 1 | zone 2 | zone 3 | zone 4 | zone 5 | Head | Die |
|---|---|---|---|---|---|---|---|
| °C. | 35 | 80 | 175 | 175 | 180 | 195 | 195 |

After extrusion, the coated tube was cut into 35 cm long samples. The UV cured samples were swelled in a 0.9% saline solution for at least 24 hours. The gel cohesion and adhesion of the layers to the tube were subjectively evaluated.

The adhesion to the tube was improved for the first three compounds when they were UV cured with the highest intensity. Compound A with the lowest amount of Irgacure 2959 bound to aliphatic, hydrophobic polyurethanes needed the highest UV intensity treatment to adhere acceptably to the tube. Compound D with the highest amount of Irgacure 2959 bound to aliphatic, hydrophobic polyurethanes could be cured with much lower UV intensity to adhere properly to the tube

| Compound number | % Irgacure 2959 bounded aliphatic, hydrophobic polyurethanes | 80% UV curing intensity | | 100% UV curing intensity | |
|---|---|---|---|---|---|
| | | Gel cohesion (1-6) | Adhesion to substrate (1-4) | Gel cohesion (1-6) | Adhesion to substrate (1-4) |
| A | 0.5 | 1 | 1 | 2 | 2 |
| B | 2.0 | 6 | 2 | 6 | 2 |
| C | 3.0 | 6 | 3 | 6 | 4 |
| D | 6.0 | 6 | 4 | 6 | 4 |

The invention claimed is:

1. A method for the preparation of a medical device element, said method comprising the steps of:

(i) providing a prefabricated shaped article and/or a thermoplastic substrate polymer;

(ii) providing a coating composition having, in the absence of ethylenically unsaturated functionality:

(a) a polymer constituent, wherein the polymer constituent is (I) one or more poly(ethylene oxide)s each having a weight average molecular weight greater than 10,000 Da optionally in combination with (II) one or more non-thermoplastic hydrophilic polymers, said one or more poly(ethylene oxide)s constituting at least 50% by weight of said polymer constituent, and (b) one or more scaffolds, each scaffold being an organic compound having a weight average molecular weight in the range of 100-10,000 Da and carrying a plurality of photo-initiator moieties covalently linked thereto and/or covalently incorporated therein, wherein the photo-initiator moieties constitute 0.01-20% by weight of the combined amount of the polymer constituent and the one or more scaffolds and wherein ethylenically unsaturated functionality is absent in the coating composition;

(iii) extruding, injection moulding or powder coating the coating composition of step (ii) on the prefabricated shaped article and/or the thermoplastic substrate polymer of step (i) so as to provide the medical device element of said prefabricated shaped article and/or said substrate polymer having thereon a layer of said coating composition, wherein, when both of said prefabricated shaped article and said substrate polymer are present, said prefabricated shaped article has thereon a layer of said substrate polymer; and (iv) irradiating the coating composition with UV or visible light so as to covalently cross-link said coating composition.

2. The method according to claim 1, wherein the polymer constituent is the one or more poly(ethylene oxide)s.

3. The method according to claim 1, wherein the polymer constituent is the one or more poly(ethylene oxide)s in combination with the one or more non-thermoplastic hydrophilic polymers.

4. The method according to claim 3, wherein the one or more non-thermoplastic hydrophilic polymers are selected from the group consisting of poly(N-vinyl pyrrolidone), poly(acrylic acid), polyoxazoline, and copoly(methyl vinyl ether/maleic anhydride).

5. The method according to claim 1, wherein the scaffold is selected from polyethylene glycols, poly(styrene-co-maleic anhydride)s, aliphatic polyether urethanes, polyetheramines, and polyesters.

6. The method according to claim 1, wherein the poly(ethylene oxide) has an average molecular weight in the range of 100,000 to 8,000,000 Da.

7. The method according to claim 1 wherein the coating composition consists of 20-99.99% by weight of the one or more poly(ethylene oxide)s (PEO), 0-10% by weight of one or more plasticizers, 0.01-80% by weight of the one or more scaffolds, and
0-5% by weight of other components.

8. The method according to claim 1, wherein the coating composition consists of:
   40-94% by weight of the one or more poly(ethylene oxide)s (PEO),
   5-30% by weight of the one or more non-thermoplastic hydrophilic polymers,
   0-10% by weight of one or more plasticizers,
   1-40% by weight of the one or more scaffolds, and
   0-5% by weight of other components.

9. The method according to claim 1, wherein a prefabricated shaped article is provided in step (i), and wherein step (iii) involves extruding, injection moulding or powder coating the coating composition of step (ii) on the prefabricated shaped article of step (i) so as to provide the medical device element of said prefabricated shaped article having thereon a layer of said coating composition.

10. The method according to claim 1, wherein a thermoplastic substrate polymer is provided in step (i), and wherein step (iii) involves extruding or injection moulding the coating composition of step (ii) together with the thermoplastic substrate polymer of step (i) so as to provide the medical device element of said thermoplastic substrate polymer having thereon a layer of said coating composition.

11. The method according to claim 1, wherein a prefabricated shaped article and a thermoplastic substrate polymer are provided in step (i), and wherein step (iii) involves extruding, injection moulding or powder coating the coating composition of step (ii) on the prefabricated shaped article together with the thermoplastic substrate polymer of step (i) so as to provide the medical device element of said prefabricated shaped article and said thermoplastic substrate polymer, said prefabricated shaped article having thereon a layer of said thermoplastic substrate polymer and said thermoplastic substrate polymer having thereon a layer of said coating composition.

12. The method according to claim 1, wherein the poly(ethylene oxide) has an average molecular weight in the range of 200,000 to 4,000,000 Da.

* * * * *